(12) United States Patent
Kriesel

(10) Patent No.: US 6,485,462 B1
(45) Date of Patent: Nov. 26, 2002

(54) FLUID DELIVERY DEVICE WITH HEAT ACTIVATED ENERGY SOURCE

(75) Inventor: Marshall S. Kriesel, Saint Paul, MN (US)

(73) Assignee: Science Incorporated, Bloomington, MN (US)

(*) Notice: Subject to any disclaimer, the term of this patent is extended or adjusted under 35 U.S.C. 154(b) by 111 days.

(21) Appl. No.: 09/645,815

(22) Filed: Aug. 24, 2000

Related U.S. Application Data

(60) Continuation-in-part of application No. 09/387,447, filed on Sep. 1, 1999, now Pat. No. 6,174,300, which is a division of application No. 08/919,147, filed on Aug. 27, 1997, now Pat. No. 5,961,492.

(51) Int. Cl.[7] .......................... A61M 37/00; A61K 9/22
(52) U.S. Cl. ..................... 604/132; 604/890.1
(58) Field of Search ................. 604/131, 132, 604/151, 153, 185, 257, 259, 262, 67, 90, 890.1, 892.1; 128/DIG. 1

(56) References Cited

U.S. PATENT DOCUMENTS

| | | |
|---|---|---|
| 3,527,220 A | 9/1970 | Summers |
| 3,692,027 A | 9/1972 | Ellinwood, Jr. |
| 3,731,681 A | 5/1973 | Blackshear et al. |
| 3,951,147 A | 4/1976 | Tucker et al. |
| 4,140,122 A | 2/1979 | Kuhl et al. |
| 4,221,219 A | 9/1980 | Tucker |
| 4,350,155 A | 9/1982 | Thompson |
| 4,679,561 A | 7/1987 | Doss |
| 4,692,147 A | 9/1987 | Duggan |
| 4,717,800 A | 1/1988 | Suzuki |
| 4,732,930 A | 3/1988 | Tanaka et al. |
| 4,978,338 A | 12/1990 | Melsky et al. |
| 5,263,323 A | 11/1993 | Maus et al. |
| 5,368,570 A * | 11/1994 | Thompson et al. ......... 604/132 |
| 5,403,893 A | 4/1995 | Tanaka et al. |
| 5,443,450 A | 8/1995 | Kratoska et al. |
| RE35,068 E | 10/1995 | Tanaka et al. |
| 5,505,706 A | 4/1996 | Maus et al. |
| 5,575,770 A | 11/1996 | Melsky et al. |
| 5,616,127 A | 4/1997 | Tanaka et al. |
| 5,797,898 A | 8/1998 | Santini et al. ............ 604/890.1 |
| 5,800,421 A | 9/1998 | Lemelson ................ 604/891.1 |
| 5,820,589 A | 10/1998 | Torgerson et al. |
| 5,830,207 A | 11/1998 | Leeb et al. .............. 604/890.1 |
| 5,840,069 A | 11/1998 | Robinson .................... 604/131 |
| 5,876,741 A | 3/1999 | Ron |
| 5,935,593 A | 8/1999 | Ron et al. |
| 5,976,109 A | 11/1999 | Heruth ........................ 604/140 |
| 6,001,090 A | 12/1999 | Lenhart .................... 604/890.1 |
| 6,030,442 A | 2/2000 | Kabra et al. |
| 6,048,328 A | 4/2000 | Haller et al. |

FOREIGN PATENT DOCUMENTS

| | | |
|---|---|---|
| WO | WO96/02276 | 2/1996 |
| WO | WO96/40032 | 12/1996 |

OTHER PUBLICATIONS

J. Biomater, Sci. Polymer Edn, vol. 5, No. 5, pp485–496, "Electro–driven chemomechanical polymer gel as an intelligent soft material" Oct. 22, 1992.

T. Tanaka, Science, "Reports—Collapse of Gels in an Electric Field", 1980.

T. Shiga, Proc. Japan Acad., 74, Ser. B (1998), vol. 74(B), "Deformation & Viscoelastic Behavior of Polymer Gels in Electric Fields", Jan. 12, 1998.

(List continued on next page.)

*Primary Examiner*—Anhtuan T. Nguyen
(74) *Attorney, Agent, or Firm*—Schwegman, Lundberg, Woessner & Kluth, P.A.

(57) ABSTRACT

An implantable fluid delivery apparatus for infusing medicinal fluids into a patient that includes a novel heat responsive polymer gel material that, upon being heated by a heating coil uniquely functions as an internal energy source for expelling the medicinal fluids from the device.

33 Claims, 27 Drawing Sheets

OTHER PUBLICATIONS

K. Kajiwara Et Al, News and Views, "Polymers—Synthetic Gels on the Move" Jan. 16, 1992, pp. 208&209, vol. 335.

I.C. Kwon et al, "Characteristics of Charged Networks Under an Electric Stimulus", Journal of Polymer Science: PartB:Polymer Physics, vol. 32, pp. 1085–1092.

J. Biomater, "Science Polymer" edition, "Journal of Biomaterials Science".

Journal of Applied Polymer Science article entitled Electric Current Sensitive Polymers. Reversible Bending of Rpd–Shaped Acrlymide Gel.

Journal of Applied Polymer Science by Shiga et al regarding of bending polymer.

Shirahama et al, Elsevier regarding interaction of sufactant with polymer gel binding isotherm HO_Sheng Lin, dissertation regarding various electric polymer gels.

Osada. Science–Cem, J. Macromol J.P. Gong and Y. Osada "Electrical Responses of Polymer Gels".

Physical Review Letters, vol. 45, No. 20 Phase Transitions in Ionic Gels.

Physical Review Letters, vol. 40, No. 12 Collapse of Gels and the Critical Endpoint.

* cited by examiner

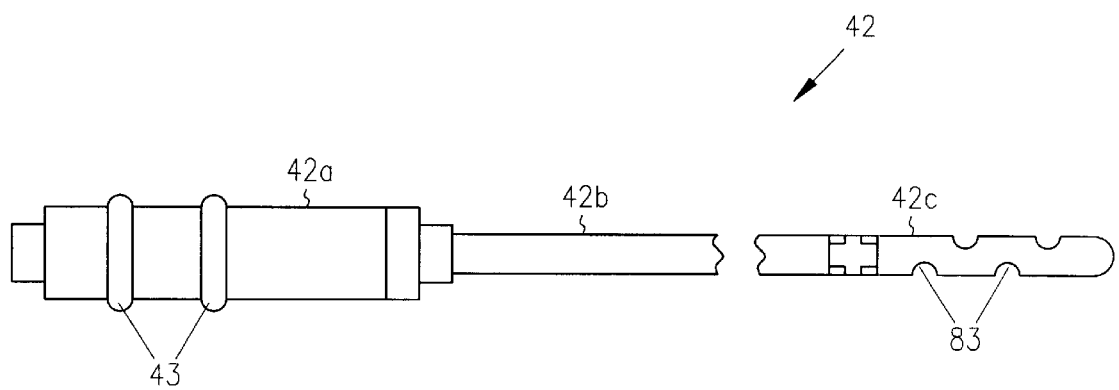
FIG. 9
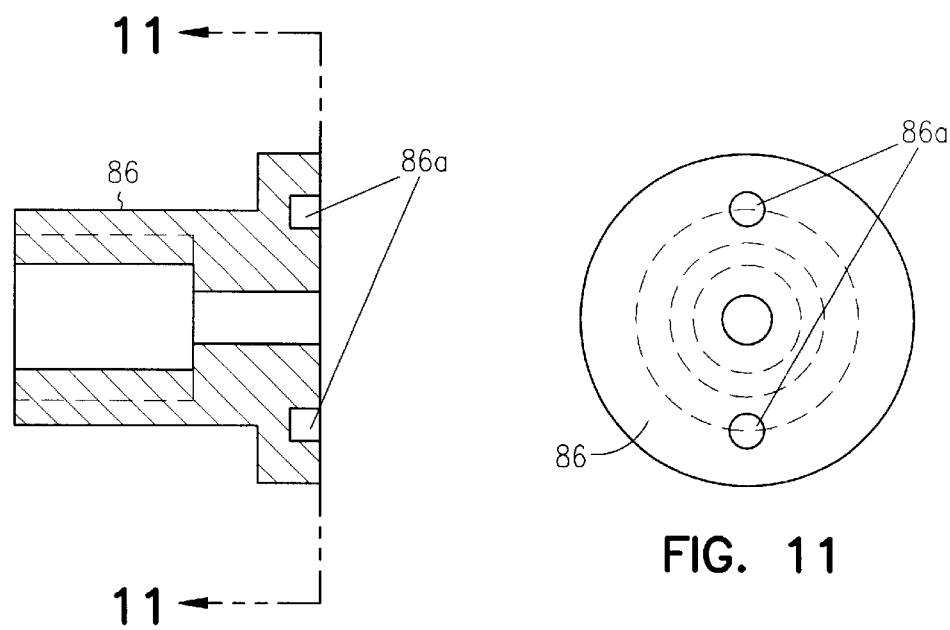
FIG. 11
FIG. 10

FLUID DELIVERY DEVICE WITH HEAT ACTIVATED ENERGY SOURCE

This is a Continuation-In-Part of application Ser. No. 09/387,447 filed Sep. 1, 1999; now U.S. Pat. No. 6,174,300 which is a Divisional application of application Ser. No. 08/919,147 filed Aug. 27, 1997, now U.S. Pat. No. 5,961, 492.

BACKGROUND OF THE INVENTION

FIELD OF THE INVENTION

The present invention relates generally to fluid delivery devices. More particularly, the invention concerns an improved apparatus having a heat activated energy source for infusing medicinal agents into an ambulatory patient at specific rates over extended periods of time.

DISCUSSION OF THE INVENTION

The oral route is the most frequent route of drug administration. Oral administration is relatively easy for most patients and rarely causes physical discomfort. However, many medicinal agents require a parenteral route of administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow means coupled with electronic based controls and typically involve the use of intravenous administration sets and the familiar bottle or solution bag suspended above the patient. Such methods are cumbersome, imprecise and, generally non-ambulatory requiring bed confinement of the patient. Periodic monitoring of the apparatus by the nurse or doctor is required to detect malfunctions of the infusion apparatus.

Devices of the character from which liquid is expelled from a relatively thick-walled bladder by internal stresses within the distended bladder have also been suggested for infusion of medicaments. For example, such bladder, or "balloon" type devices, are described in U.S. Pat. No. 3,469,578, issued to Bierman and in U.S. Pat. No. 4,318, 400, issued to Perry.

A family of highly unique fluid delivery devices has been developed by the present inventor. These novel devices make use of recently developed elastomeric films, expandable foams and similar materials, which, in cooperation with a base define a fluid chamber that contains the fluid to be dispensed. The elastomeric film membrane or the expandable member controllably forces fluid within the chamber into outlet fluid flow channels provided in the device. Elastomeric film membrane devices are described in detail in U.S. Pat. No. 5,205,820 issued to the present inventor. U.S. Pat. No. 5,468,226, also issued to the present inventor, describes various types of expandable cellular elastomers and elastomeric foams used as the energy source of the fluid delivery device for expelling fluid from various physical forms of the fluid delivery device. Because of the pertinence of Pat. Nos. 5,205,820 and 5,468,226, these patents are hereby incorporated herein by reference in their entirety as though fully set forth herein. U.S. Pat. No. 5,961,492 entitled Fluid Delivery Device with Temperature Controlled Energy Source, in which the present inventor is named as a co-inventor, is also incorporated by reference as though fully set forth herein.

The apparatus of the present invention, comprises a unique implantable unit that makes use of novel light activated expansive material as an energy source. The apparatus of the invention can be used for the continuous infusion of a variety of beneficial agents as, for example, heparin, morphine, insulin and like agents.

SUMMARY OF THE INVENTION

It is an object of the present invention to provide a technically advanced, fluid delivery apparatus for infusing medicinal fluids into a patient that is of a compact, low profile, laminate construction. More particularly, it is an object of the invention to provide an apparatus of such a character which is implantable into the patient's body and includes a novel expanding polymer gel material which uniquely functions as an internal energy source for expelling the medicinal fluids from the device.

Another object of the invention is to provide an implantable fluid delivery apparatus that can be used for the precise infusion of various pharmaceutical fluids into the patient at controlled rates over extended periods of time.

Another object of the invention is to provide an apparatus of the forementioned character which is of a simple construction and is highly reliable in operation.

Another object of the invention is to provide an apparatus that embodies as its stored energy source, a soft, pliable, semi-solid, heat-expandable mass which is heated either by the patient's body temperature or by an external stimulus in a manner to controllably expel fluid from the device.

Another object of the invention is to provide an apparatus as described in the preceding paragraph in which the heat expandable mass is specifically tailored to provide precise, predictable protocol delivery of the medicinal agent stored within the reservoir of the device.

A further object of the invention is to provide a low profile, readily implantable fluid delivery device of laminate construction which can meet even the most stringent fluid delivery tolerance and flow signature requirements.

Another object of the invention is to provide an apparatus of the character described which is responsive to an external source of stimulation such as heat, and includes a three-dimensional polymer network which functions as a stored energy source that can be constructed from various types of polymeric conformable materials such as phase transition gels.

Another object of the invention is to provide stored energy sources of the character described in the preceding paragraph which comprise blends or laminate constructions of phase transition gels that will enable the achievement of multi-rate delivery protocols.

Another object of the invention is to provide a device of the character described that includes fill means for filling the reservoir of the device.

Another object of the invention is to provide an implantable fluid delivery device as described in the preceding paragraphs that includes physiological sensor means for sensing physiological changes in the patient's body.

Another object of the invention is to provide an apparatus of the character described which includes a novel, combination filter and rate control assemblage disposed intermediate the fluid reservoir and the outlet port of the device or intermediate outlet port of the device and the infusion means.

Another object of the invention is to provide an apparatus of the character described which, due to its unique construction, can be manufactured inexpensively in large volume by automated machinery.

Another object of the invention is to provide an implantable fluid delivery device that includes a stored energy source comprising an expandable gel that is stimulated by a heating coil disposed proximate the gel.

Another object of the invention is to provide a device as described in the preceding paragraphs in which the heated coil is heated by a radio frequency signal. More particularly, the heating coil is coupled with a receiving antenna that is inductively coupled with a transmitting antenna disposed externally of the patient's body.

Other objects of the invention will become apparent from the discussion which follows.

BRIEF DESCRIPTION OF THE DRAWINGS

FIG. 9 is a top plan view of the cannula assembly of the apparatus shown in FIG. 1.

FIG. 10 is a cross-sectional view of the cannula closure member that secures the cannula assembly in position relative to the outlet port of the apparatus.

FIG. 11 is a view taken along lines 11—11 of FIG. 10.

DESCRIPTION OF THE INVENTION

Figure 1:
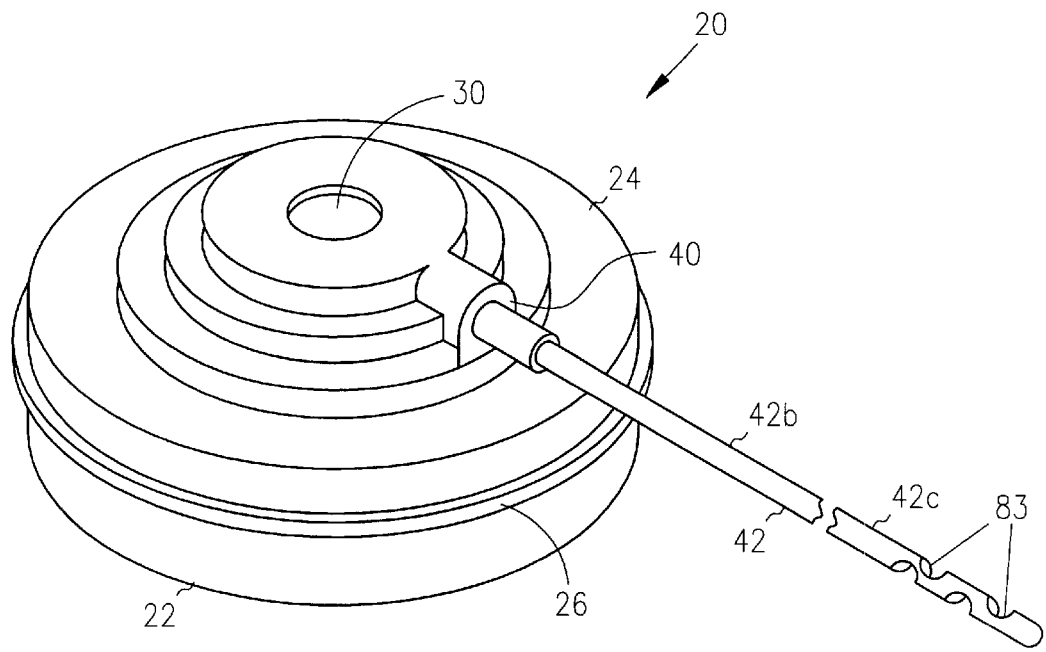
FIG. 1 is a generally perspective view of one form of implantable medicament delivery device of the invention.
Figure 2:
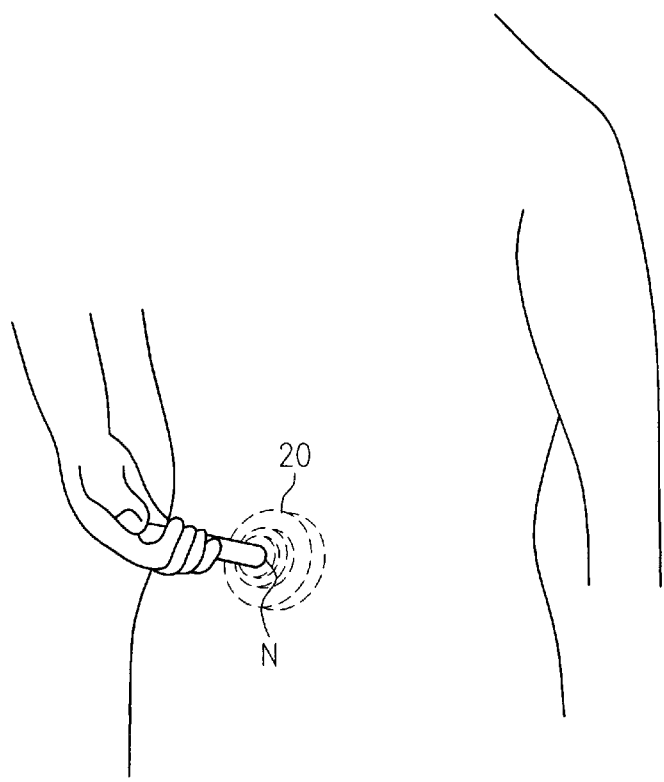
FIG. 2 is a generally perspective, illustrative view showing the delivery device of FIG. 1 implanted within the patient's body and illustrating in the filling of the reservoir of the device using a conventional hypodermic syringe
Figure 3:
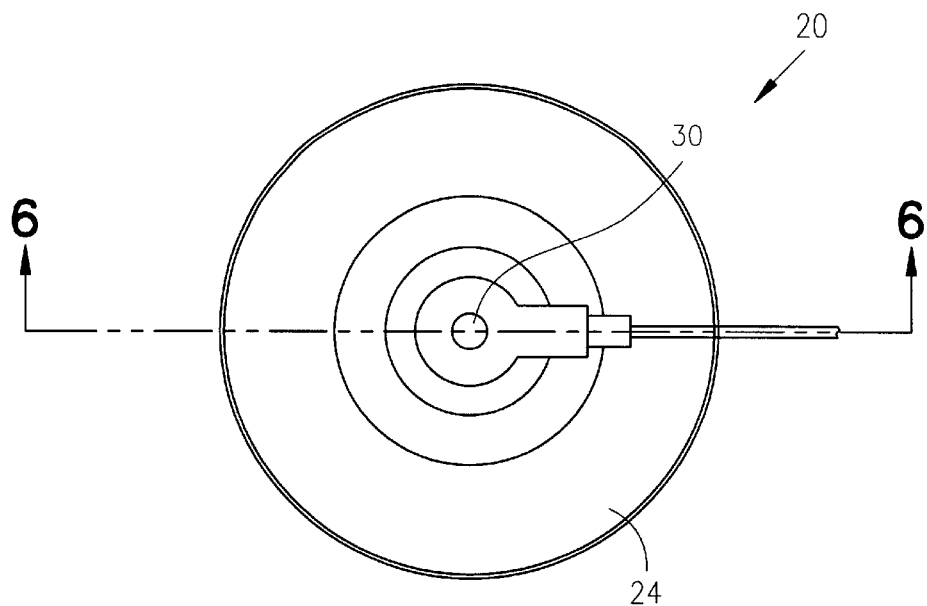
FIG. 3 is a top plan view of the fluid delivery apparatus of the invention shown in FIG. 1.
Figure 4:
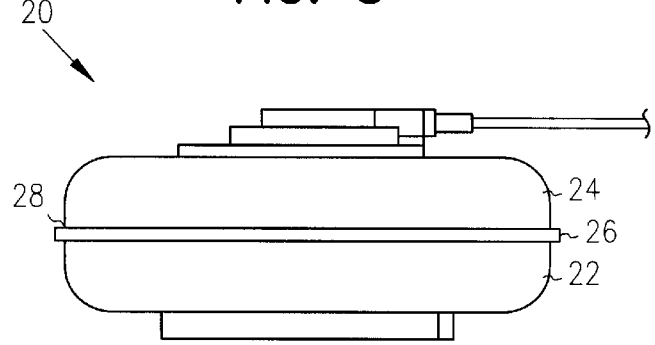
FIG. 4 is a side view of the device shown in FIG. 3.

Referring to the drawings and particularly to FIGS. 1 through 18, one form of the apparatus of the invention is there shown and generally designated by the numeral 20. As indicated in FIG. 2 of the drawings, this embodiment of the invention, is specially designed to be implanted into the body of the patient. As shown in FIGS. 1 through 8, the apparatus here comprises a titanium base 22 and a titanium cover 24 that can be joined together by welding at interface 26 to form the hollow, hermetically sealed housing 28 of the device.

Figure 6:
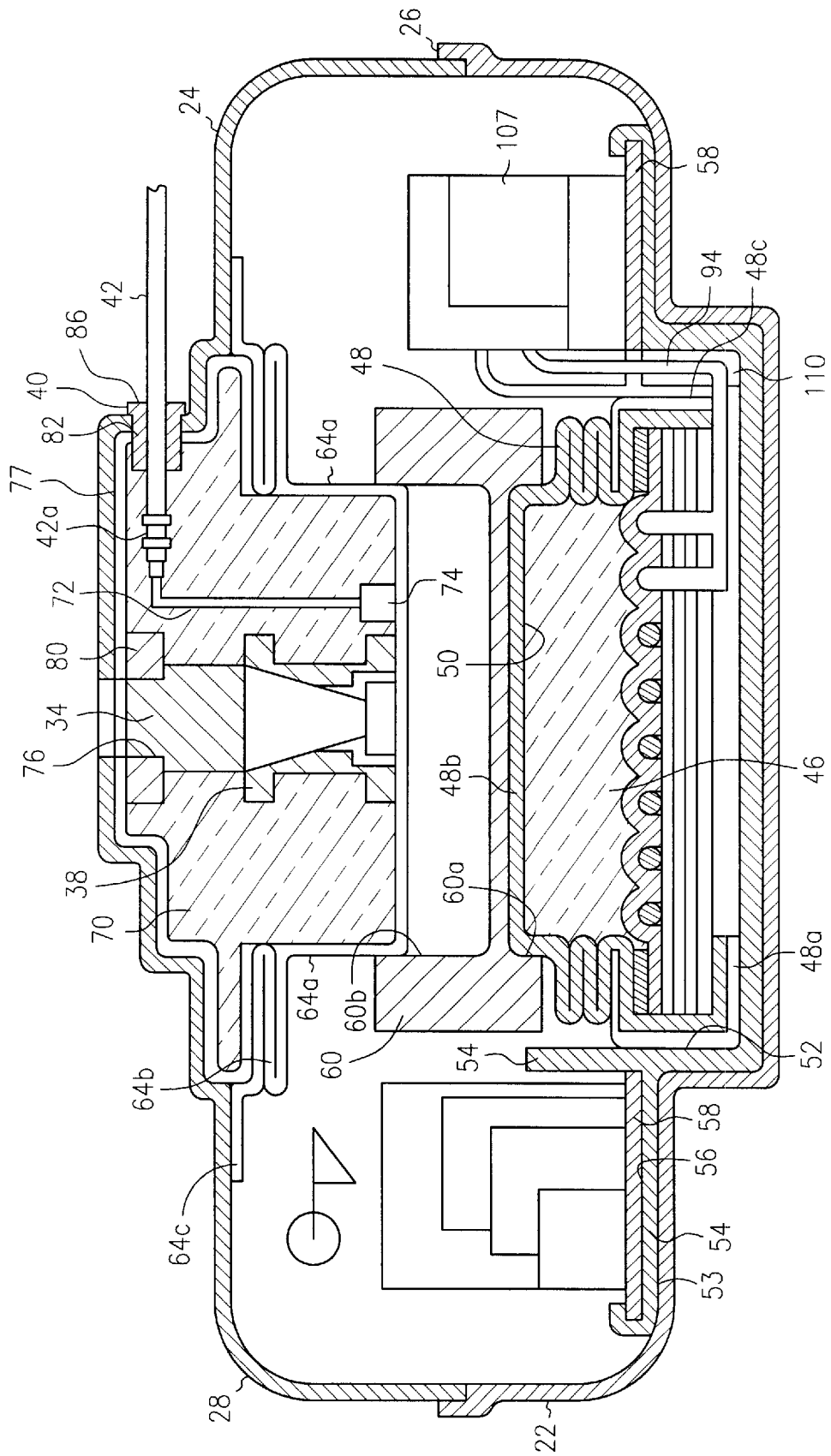
FIG. 6 is an enlarged cross-sectional view taken along lines 6—6 of FIG. 3.
Figure 7:
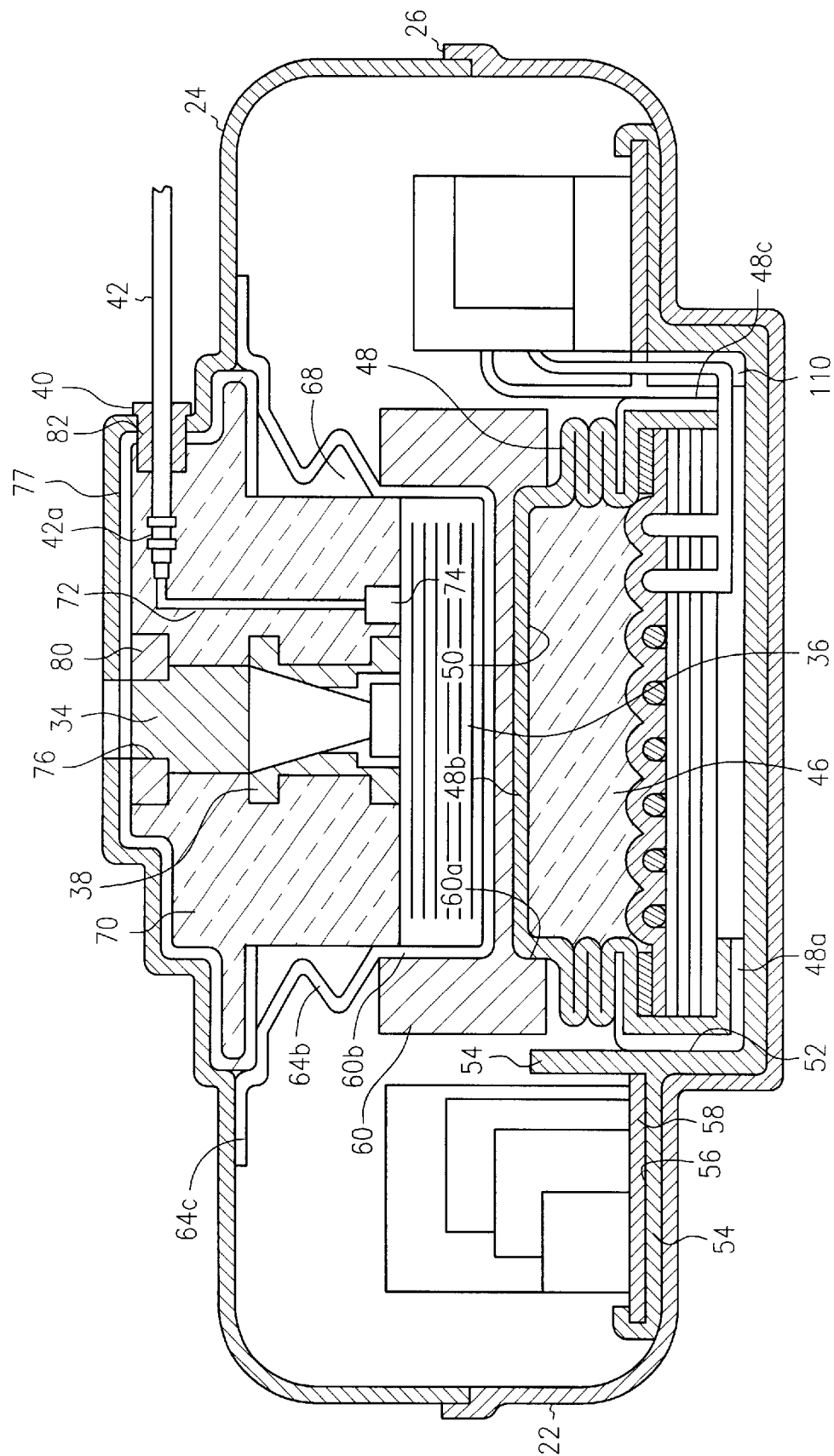
FIG. 7 is a cross-sectional view similar to FIG. 6, but showing the reservoir in a filled condition.
Figure 8:
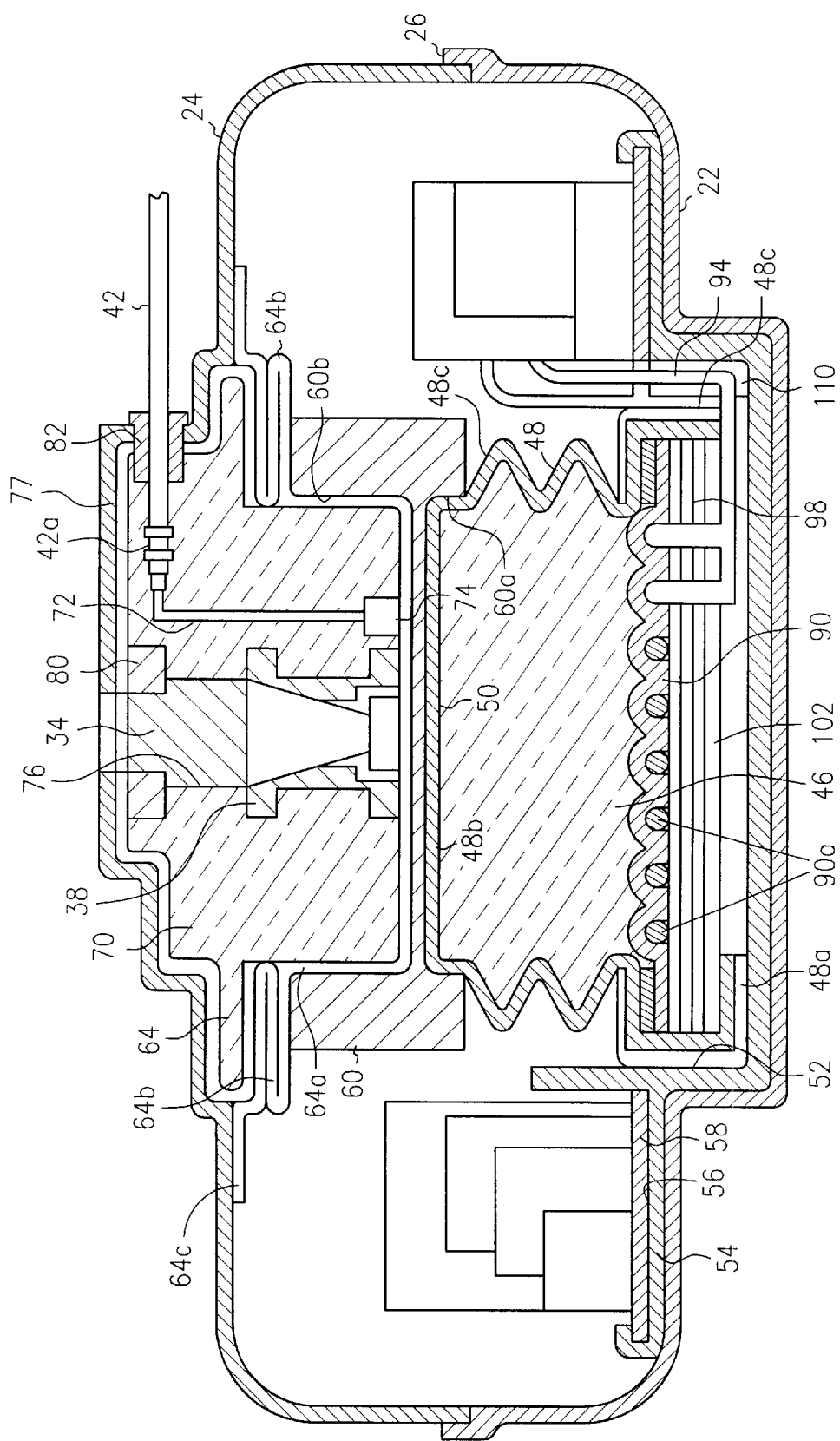
FIG. 8 is a cross-sectional view similar to FIG. 7, but showing the expandable gel in an expanded configuration following delivery of all of the medicament to the patient.

Preferably the device is adapted to be implanted within the patient's body at a location immediately below a layer of skin and includes fill means for filling the device reservoir. The fill means here comprises an access port 30 formed in cover 24 that can be accessed by a hypodermic needle "N". With the arrangement shown in FIGS. 1 and 2, the hypodermic needle can be inserted through the skin to introduce, via the access port, a quantity of liquid medicament such as heparin, morphine, insulin or like medicament through a septum 34, which also forms a part of the fill means, into a medicament reservoir 36. A tapered needle guide 38 disposed within the ullage means of the device supports septum 34 and guides the entry of the hypodermic needle toward reservoir 36 (FIGS. 6 and 7).

During operation, the medicament is delivered from the delivery device via a cannula port 40 to which a delivery means for delivering fluid to the patient is attached. The delivery means here comprises a cannula assembly 42 (FIGS. 1 and 7). Cannula assembly 42 is strategically positioned at the time of implant to deliver the medicament to a selected therapeutic site within the patient's body by means of a suitable porous tip cannula, the character of which will presently be described.

Housing 28 houses the novel heat activated stored energy source of the invention which functions to cause the fluids contained within the sealed reservoir 36 (FIG. 7) of the device, the character of which will presently be described, to flow outwardly thereof through cannula assembly 42. The heat activated means or stored energy source is provided in the form of a heat activated expandable polymer mass 46 which is disposed within an expandable, hermetically sealed structure or metal bellows assembly 48 that is mounted within housing 28 in the manner best seen in FIGS. 6, 7, and 8. Expandable mass 46 can take several forms including a laminate construction made up of layers of masses and various composition which cooperate to function as the energy source of the apparatus. Alternatively, mass 46 can comprise a single mass in semisolid form such as a gel having certain novel attributes which will presently be described.

Figure 12:
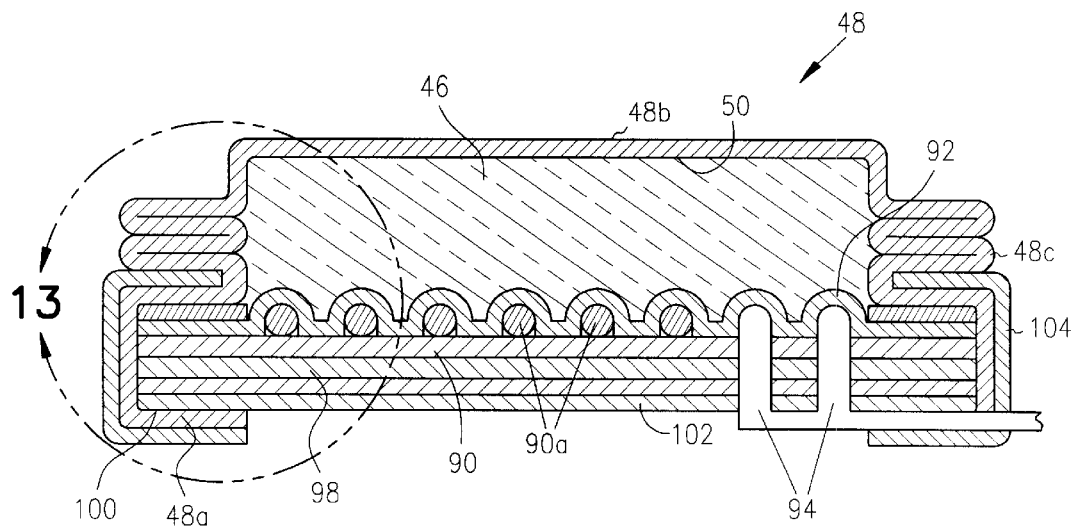
FIG. 12 is a cross-sectional view of the bellows assembly that houses the expandable gel, the heat source and the ceramic heat deflector of the apparatus.
Figure 13:
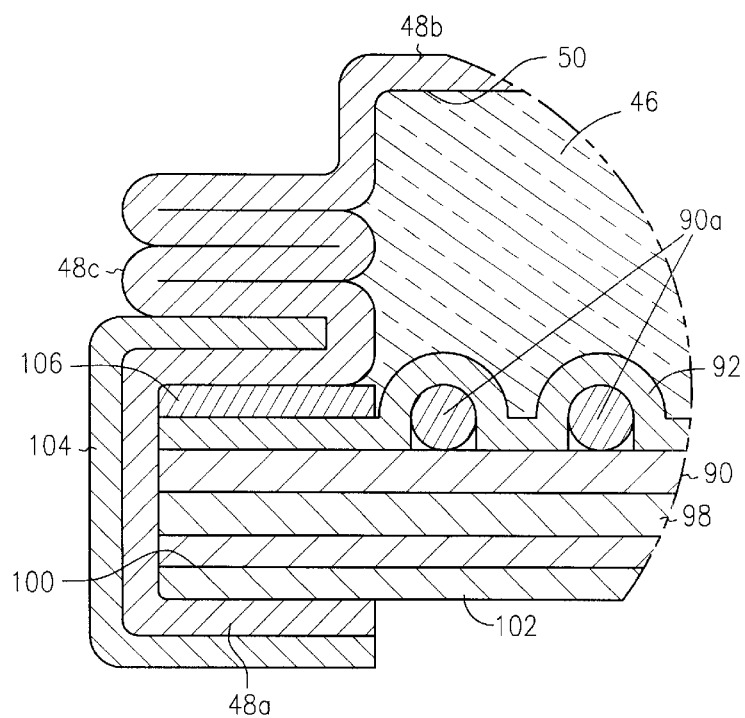
FIG. 13 is an enlarged, fragmentary, cross-sectional view of the area designated as 13 in FIG. 12. .

As best seen in FIGS. 12 and 13, bellows assembly 48 includes a base portion 48a, an upstanding, reduced diameter cover 48b and an expandable bellows-like sidewall 48c which are interconnected to define the gel receiving chamber 50. Bellows assembly 48 is closely received within a receiving chamber 52 formed in a carrier assembly 54, which is, in turn, received within base 22.

As illustrated in FIGS. 6 and 7, surrounding chamber 52 is an electronics receiving channel 56 that supports an annular shaped, printed circuit (PC) board 58 and the electronic components associated therewith, the character of which will presently be described. Upstanding cover 48b of bellows assembly 48 is closely received within the lower portion 60a of a generally annular shaped capture ring 60 (FIGS. 6 and 15) that is disposed intermediate base 22 and cover 24 of housing 28.

As best seen in FIG. 7, the base portion 64a of an expandable structure which forms the upper reservoir assembly 64 of the apparatus is receivable within the upper portion 60b of the capture ring 60. Connected to base portion 64a is a bellows-like wall 64b, which cooperates with base portion 64a to form the expandable fluid reservoir 36 of the apparatus (FIG. 7). Connected to wall 64b is a connector flange 64c that can be sealably interconnected with the lower surface of cover 24, as by welding, to form a hermetically sealed chamber 68, a portion of which comprises medicament reservoir 36 (see FIGS. 7 and 16).

Figure 16:
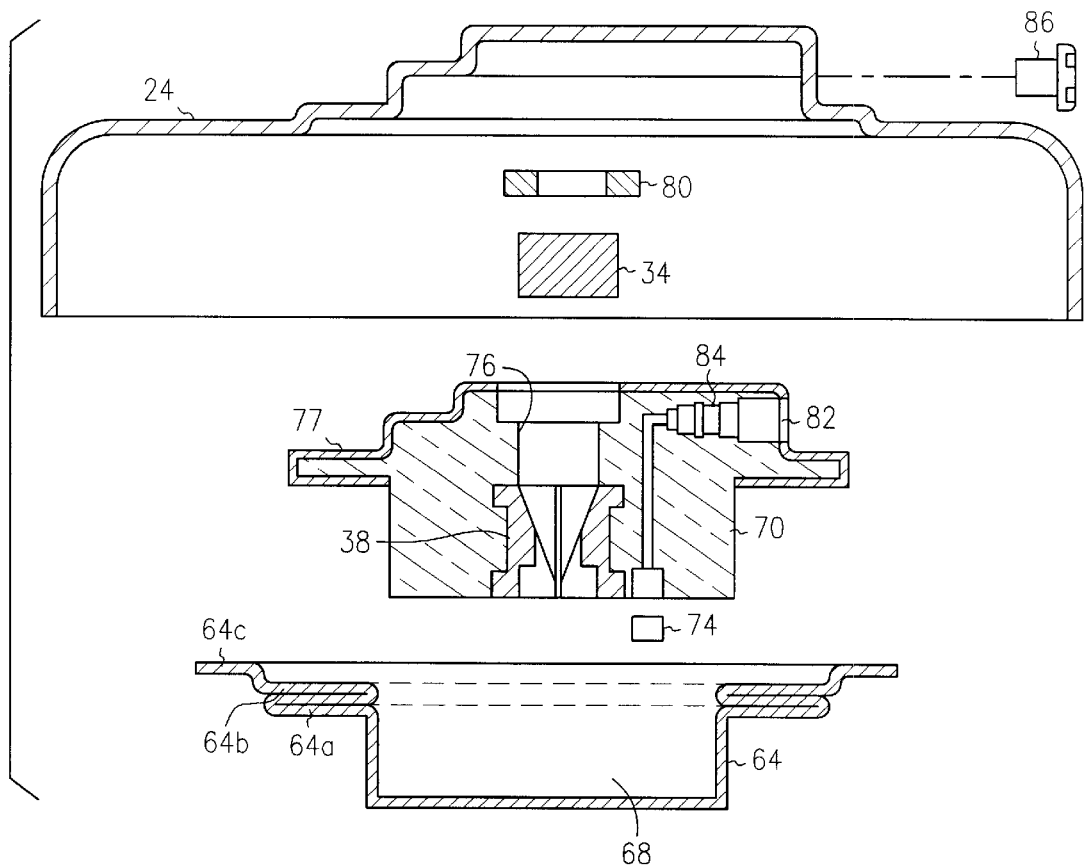
FIG. 16 is an exploded, cross-sectional view of the upper half shell of the apparatus that houses the upper reservoir bellows, the ullage and the septum assembly.

Disposed within chamber 68 is a novel co-molded plastic ullage assembly 70 which includes a fluid passageway 72 that is in communication with reservoir 36 via an impedance frit 74 and with cannula port 40. Formed within ullage assembly 70 proximate needle guide 38 is a septum receiving chamber 76 that houses septum 34 that is pierceable by the needle "N" of the hypodermic syringe used to fill reservoir 36. Ullage 70 is partially encapsulated within an elastomer 77. Septum 34 is accessible through a sealing ring 80 that is disposed proximate cover 24 (FIG. 16). Also formed within ullage assembly 70 is an internally threaded cannula connector portion 82 to which the delivery cannula assembly 42 of the apparatus can be sealably interconnected (FIGS. 10 and 11). As best seen by referring to FIG. 9, cannula assembly 42 comprises an elastomeric molded connector portion 42a that is provided with a plurality of spaced apart, rib-like protuberances 43. Connected to connector portion 42a is a hollow cannula 42b that includes a porous tip 42c that permits fluid to flow outwardly through small outlet passageways 83 formed in the porous tip 42c. Connector portion 42a is sealably receivable within the internally ribbed connector port 84 (FIG. 16). As best seen in FIG. 6, a threaded cannula closure member 86 (FIG. 10, 11 and 16), which is threadably receivable within a threaded connector port 82 formed in ullage 70 functions to hold the cannula assembly in position and to compress connector portion 42a in a manner to insure maintenance of a leak-tight seal between the cannula assembly and the device housing. An appropriate spanner wrench (not shown) can be used to engage apertures 86a (FIG. 11) to threadably interconnect member 86 with ullage 70.

Figure 14:
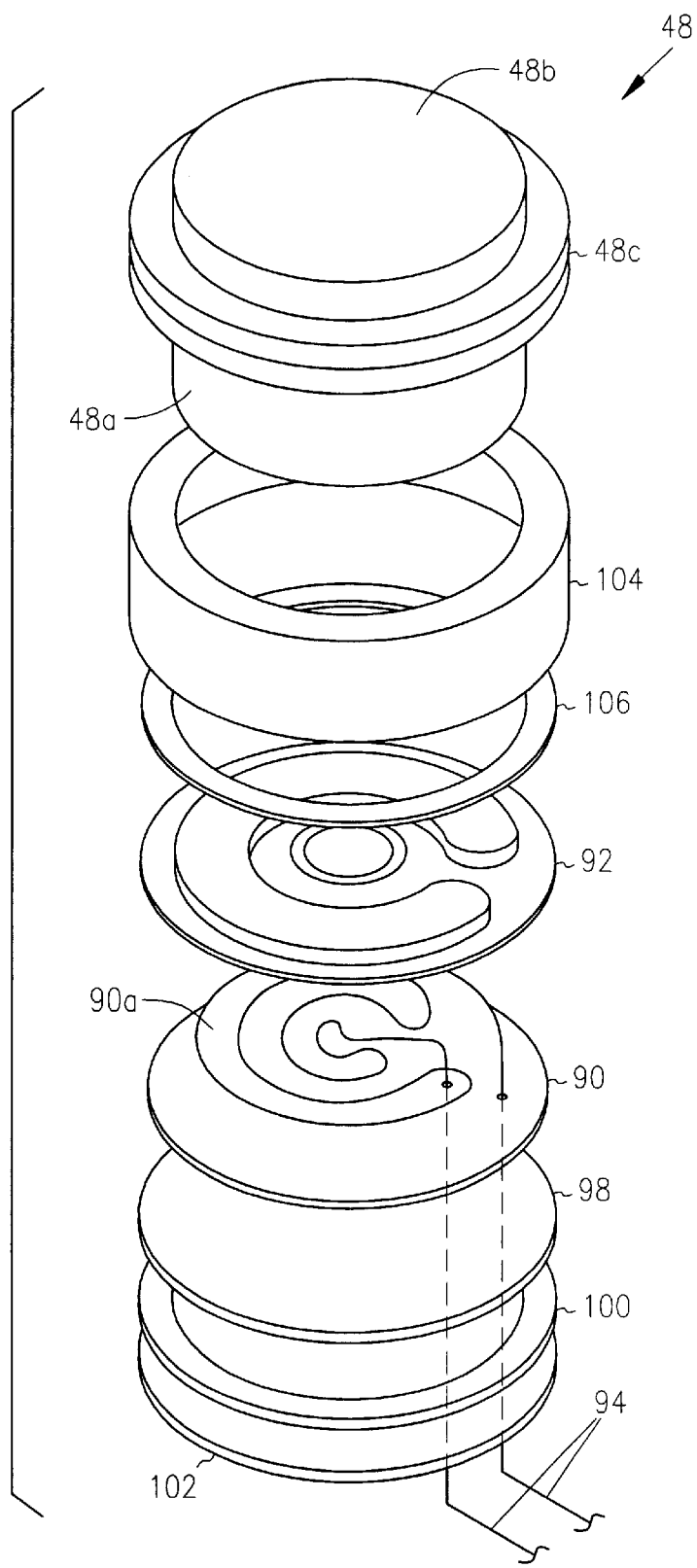
FIG. 14 is a generally perspective, exploded view of the assembly shown in FIG. 13.
Figure 15:
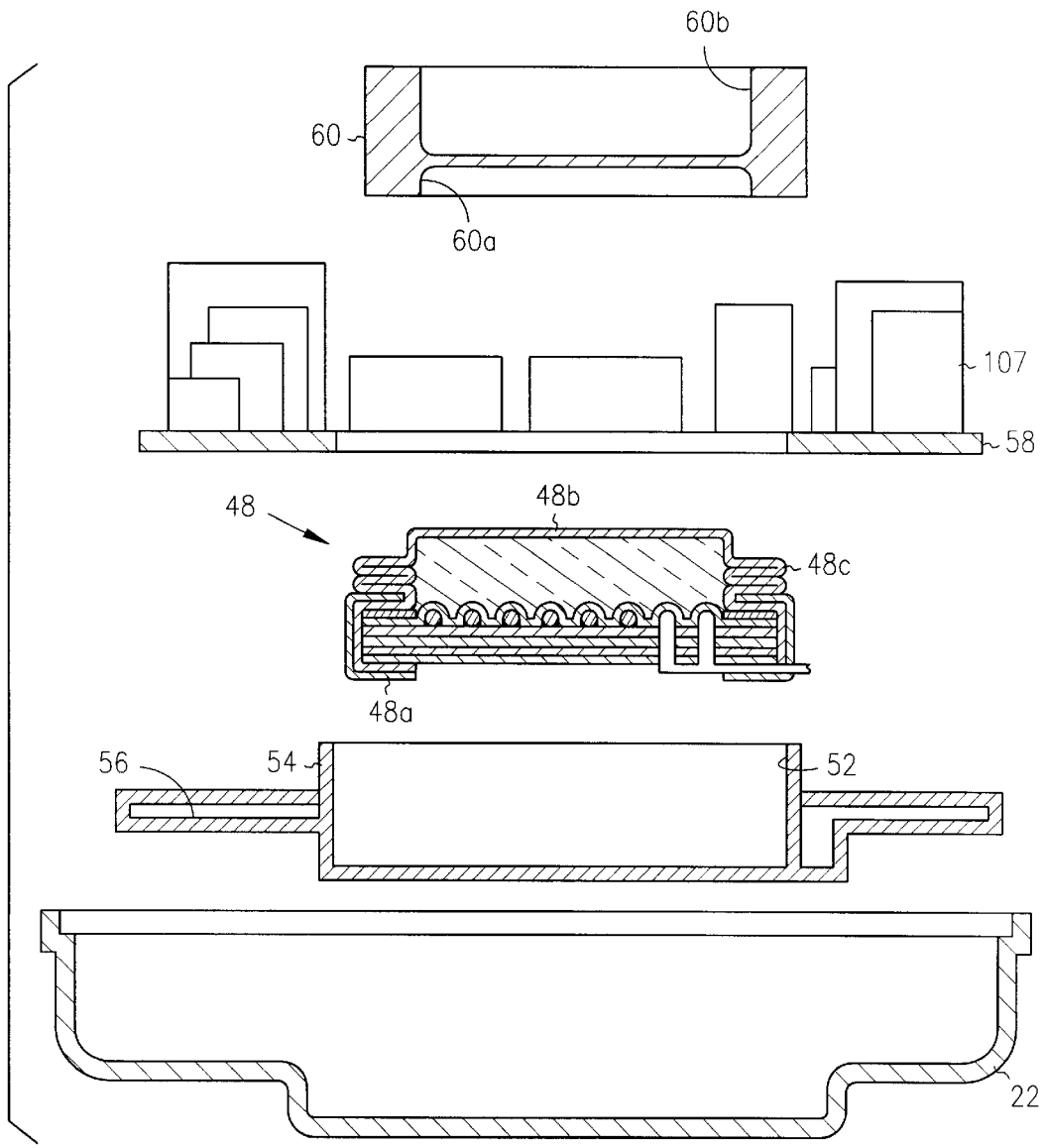
FIG. 15 is an exploded, cross-sectional view of the lower half shell of the apparatus that houses the carrier assembly, the connector ring, the bellows assembly, the expandable gel, the heat deflector, the heat source and the electronics associated therewith.

Considering next the activating means of the invention for activating the expandable mass or gel 46, this novel means here comprises a source of heat including a first, or lower heater plate 90 and a second, or upper heater plate 92, both of which are carried within bellows assembly 48. Power is supplied to the heater wires 90a of lower plate 90 by a pair of wire leads 94 that are appropriately connected to a source of electricity such as a battery 96, the character of which will presently be described. As best seen in FIGS. 13 and 14 lower heater plate 90 is supported by a ceramic heat deflector 98, which, in turn, is supported by a silicone ring seal 100. A closure plate 102 is connected to base 48a of bellows 48, as by welding, to sealably encapsulate the activating means (FIG. 13). A bellows clamp ring 104 circumscribes the lower portion of the bellows assembly in the manner indicated in FIGS. 12 and 13. To sealably position upper heater plate within the bellows assembly, a second silicone seal ring 106 is disposed between the upper surface of heater plate 92 bellows 48 (see FIG. 13). When power is supplied to heater wires 90a via leads 94, the heating plates will be controllably heated so as to controllably heat the expandable gel to a predetermined, substantially constant temperature to enable appropriate expansion thereof. The temperature to which the gel is heated is, of course, is dependent upon the type of gel being used.

Considering now, in greater detail, the novel expandable mass or gel 46, like most gels, gel or mass 46 is of a semisolid form that can advantageously be handled without external containment under ambient manufacturing conditions. From a technical viewpoint, gels are often characterized as soft solids which reside in a state between a liquid and a solid state. Frequently gels comprise a cross-linked network of long polymer molecules with liquid molecules trapped within the network. Many gels known in the prior art not only are capable of significantly large volume change in response to stimulus (phase-transition gels), but also exhibit physical characteristics that enable them to closely conform to the shape of an adjacent member such as a distendable member.

Phase transition gels best suited for use in constructing the heat expandable mass of the present invention are gels which undergo a change in polymer conformation and in so doing exhibit a large volume change at a given phase-transition condition. Unlike liquids, which exhibit a fixed temperature for state of vaporization to a known volume and with such vaporization point changing as a function of ambient pressure, the phase-transition gels in this invention are multicomponent polymers which can be made to respond with various volume changes to a singular external temperature stimuli to perform useful work.

Advantageously, the difference in volume between the expanded phase of these phase-transition gels and the contracted phase thereof can be orders of magnitude. Examples of suitable phase-transition gels are disclosed in Tanaka et al., U.S. Pat. No. 4,732,930; No. Re-35068 and U.S. Pat. No. 5,403,893. Because of the pertinence of these patents, U.S. Pat. No. 4,732,930, U.S. Pat. No. 5,403,893 and U.S. Pat. No. Re-35068 are all hereby incorporated by reference as though fully set forth herein.

While a number of the phase-transition gels described in the Tanaka et al patents can be used to construct the heat expandable stored energy means of the present invention, the ionized acrylamide gel compositions therein described are desirable in many applications because of the quite drastic volume change they exhibit in response to an external stimulus such as the body temperature of the patient. These ionized acrylamide gel compositions comprise a cross-linked, partially ionized polyacrylamide gel wherein between up to 20% of the amide groups are hydrolyzed to carboxyl groups. The gel includes a solvent of a critical concentration at which even a slight change in temperature, pH or salt concentration causes the gel to shrink or swell dramatically. As pointed out by Tanaka et al in the aforementioned patents, the particular critical concentration utilized in the gel composition depends upon the solvent employed, the temperature of the gel and the degree of hydrolysis of the gel. The gel also can contain a positive metal ion such as sodium or magnesium which has the effect of increasing the change in gel volume caused by change of solvent concentration, temperature, pH or, salt concentration.

Another form of phase-transition gel suitable for use in the apparatus of the present invention comprises interpenetrating polymer networks which include a first polymer and a second polymer wherein the second polymer interpenetrates the first polymer. Suitable first and second polymers include polymers which can interact during exposure to a phase-transition condition to thereby cause a significantly large volume change of the gel. Suitable interpenetrating polymer networks can also include more than two polymers. For example, additional polymers can be included in the network which interpenetrate the first and/or second polymers. The nature of these polymers as well as the nature of the interaction between the polymers is discussed in detail in Tanaka, U.S. Pat. No. 5,403,893, and will not here be repeated.

The responsive gels may also be reversibly responsive. For example, when such gels experience certain environmental changes, the entire gel, or a component thereof will undergo a reversible volumetric change which typically involves a shift between two equilibrium states as, for example, expanded and collapsed. This reversible volume change of the entire gel, or a component of the gel may be either continuous or discontinuous. Typically, a continuous volume change is marked by a reversible change in volume that occurs over a substantial change in environmental condition. On the other hand, the gel, or a component thereof, may undergo a discontinuous volume change in which the reversible transition from expanded to collapsed states, and back again, typically occurs over a relatively small change in environmental condition. A gel undergoing a continuous phase-transition may have a similar order of magnitude total volume change as a gel undergoing a discontinuous phase-transition.

Typically, volumetric changes in the phase transition gels result from competition between intermolecular forces, usually electrostatic in nature. Such volumetric changes are believed to be driven primarily by four fundamental forces, that is ionic, hydrophobic, hydrogen bonding and vander Waals bonding interactions, either alone or in combination. Changes in temperature most strongly affect hydrophobic interactions and hydrogen bonding.

Of particular interest is the fact that gels consisting of copolymers of positively and negatively charged groups may be formulated so that the volume change is governed by more than one fundamental force. In these gels, polymer segments typically interact with each other through ionic interactions and hydrogen bonding.

By way of summary, gels suitable for use as the stored energy sources of the present invention include various cross-linked polymers and gels which can be synthesized from the polymerization of a monomer and a cross-linking agent. More particularly, suitable gels can be made from any polymer with side groups that can react with a di-or multi-functional cross-linking molecule. However, the simplest system from which gels can be made are polymers with hydroxyl, acid or amine side groups.

By way of non-limiting example, suitable gels for use as the stored energy means may consist, in whole or in part, of polymers made by copolymerization/cross linking of monofunctional and polyfunctional polymerizable vinyl monomers. The monomer may include N, N-disubstituted acrylamides such as N,N-dialkylsubstituted acrylamides, or di-N,N substituted acrylamides where the dissubtitution form part of a ring, acrylate ethers, alkyl substituted vinyl ethers, glycol ethers, and mixtures thereof.

Exemplary polymeric gel networks thus may contain poly (N,N-dialkylacrylamide), poly(ethyl acrylate) and mixtures thereof, as well as polymers of N-alkylacrylamide (or analogous N-alkylmethacrylamide) derivatives such as N-ethylacrylamide, N-n-propylacrylamide, N-n-propylmethylacrylamide, or various acrylate copolymers.

Exemplary cross-linking agents may include ethylene glycol diacrylate (EGDA); di(ethylene glycol)bis(allyl carbonate) ("DEGBAC"); methylenebis(acrylamide) ("bis"); ethylene glycol dimethacrylate ("EGDMA"); magnesium methacrylate ("MgMA$_2$"); and mixtures thereof. Cross-linkers suitable for polymeric precursors may include diglycidyl ether, divinyl sulfone, epichlorohydrin, phosphoryl chloride, trimetaphosphate, trimethylomelamine, polyacrolein, and ceric ion redox systems, although the most preferred of these will not have active hydrogens. The cross-linking agent effects partial cross-linking of the polymer and provides a means to control the gel's mechanical strength, swelling degree, and intensity of volume change trigger by changing the cross-linking density. Cross-linking of linear polymers by chemical reagents is preferred for gels made from biological polymers such as cellulose ethers. Preferred cross-linkers for polysaccharide gels, especially cellulos ethers, are multifunctional carboxylic acids, such as adipic acid (hexanedioic acid: $HOOC(CH_2)_4COOH$), succinic acid ($HOOC(CH_2)_2COOH$), malonic acid (propanedioic acid: $CH_2(COOH)_2$, sebacic acid (decanedioic acid: $HOOC(CH_2)COOH$), glutaric acid (pentanedioic acid: $HOOC(CH_2)_3COOH$), or 1, 10 decanedicarboxylic acid.

Figure 5:
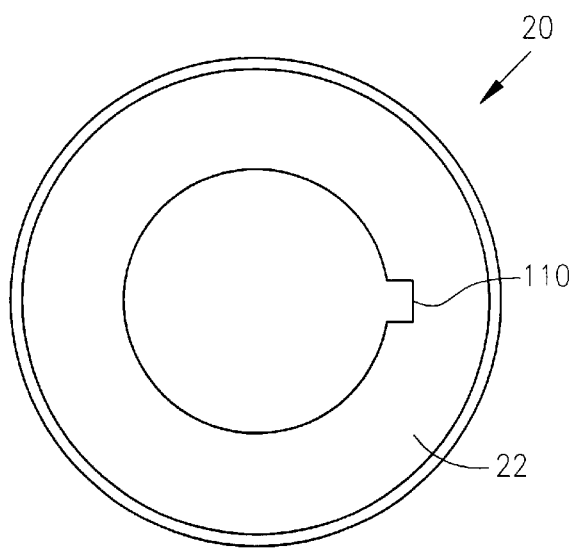
FIG. 5 is a bottom view of the device shown in FIG. 4.
Figure 17:
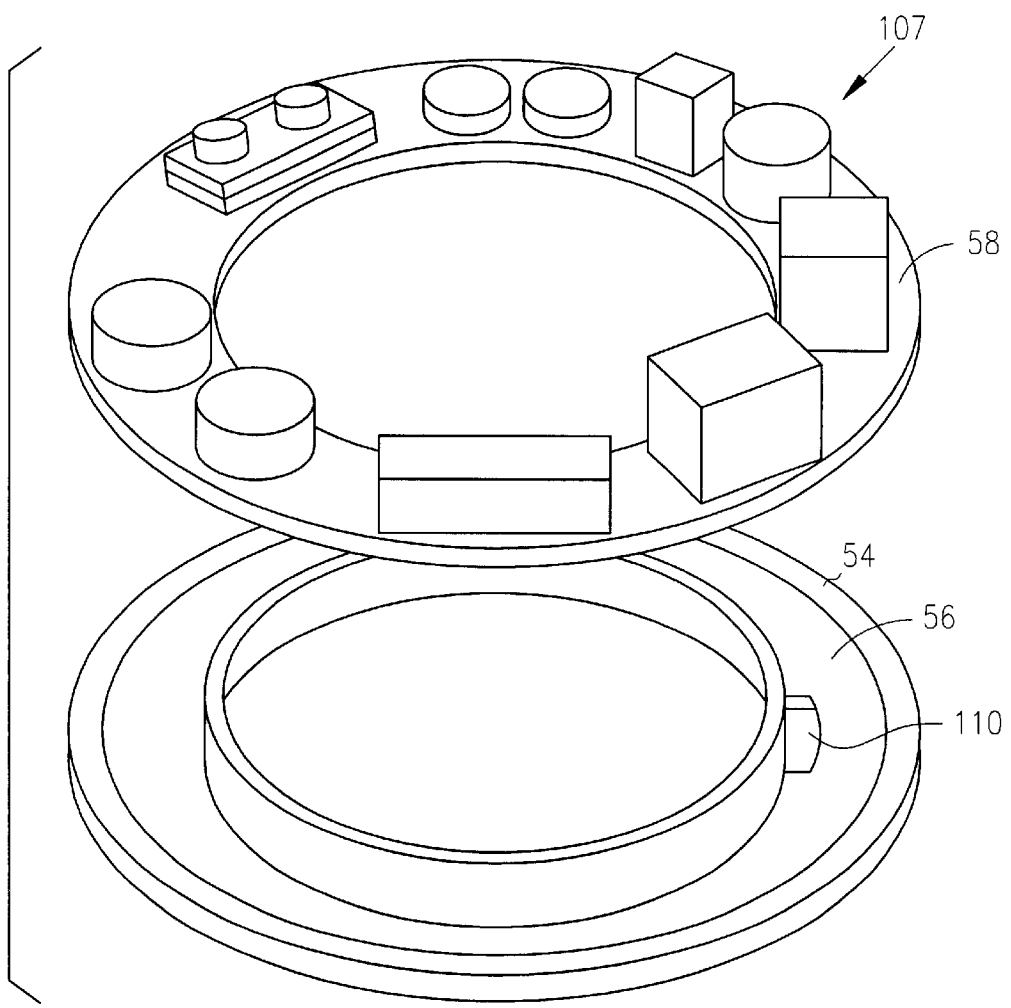
FIG. 17 is a generally perspective, exploded view of the carrier assembly, the printed circuit board and the associated electronics of the apparatus.

In using the apparatus of the invention, either before or after the reservoir has been filled in the manner shown in FIG. 7, the electronic controller can be programmed. The electronic controller here includes a mircoprocessor, a RAM/ROM memory, a power supply, feed back electronics, amplifiers, circuits, timing and control switch matrix circuits and various related circuitry (see FIG. 18). In a manner presently to be described in greater detail, the controller can be programmed to enable the precise delivery of varying dosing volumes over time in response to a programmed delivery protocol. The electronic controller can also be programmed to indicate function status to the user. The wiring leading to the electronics 107 is introduced through the electronic lead cavity 110 formed in base 22 (FIGS. 5 and 17).

Figure 18:
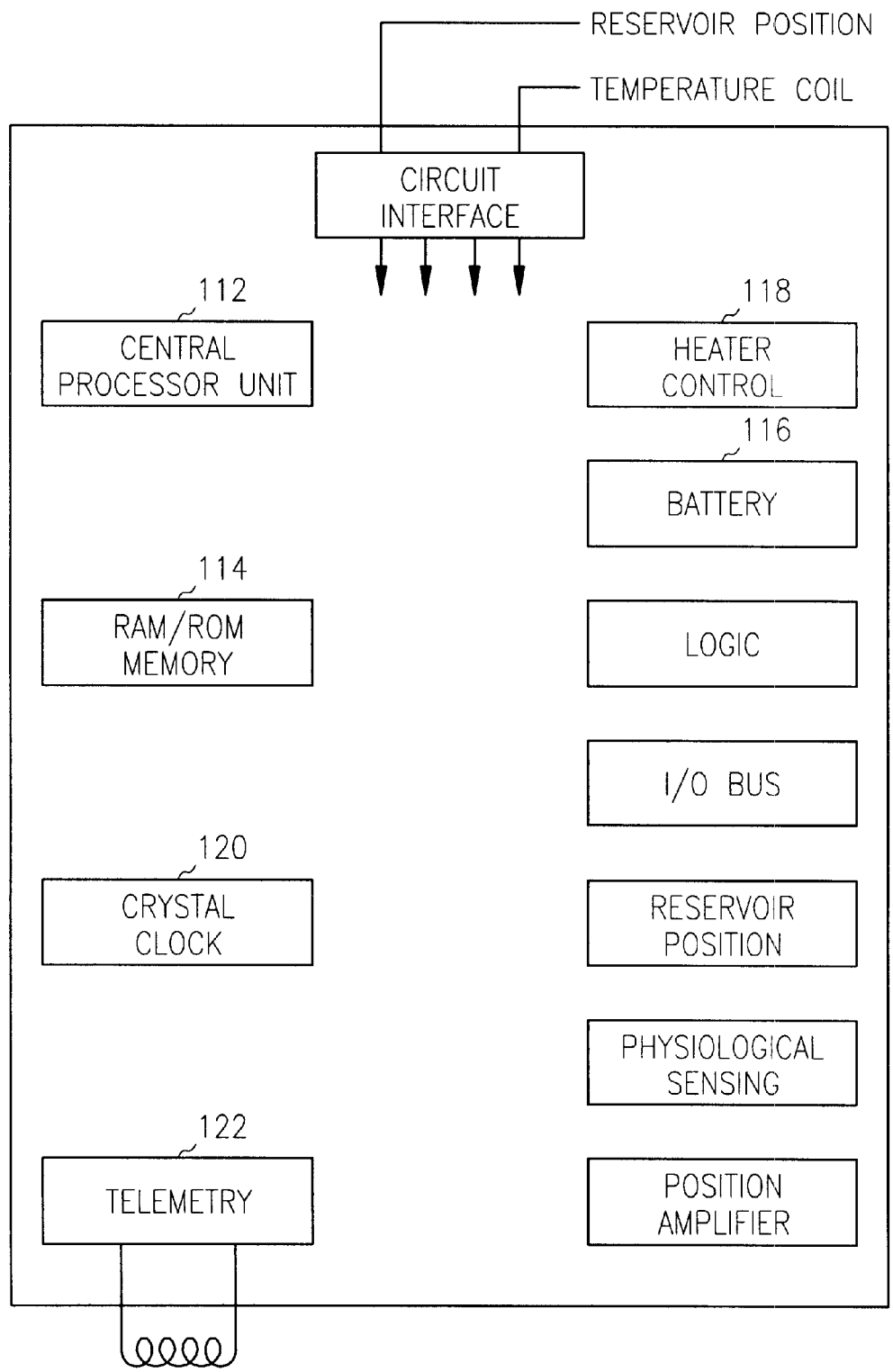
FIG. 18 is a generally diagrammatic view showing the relationship among the various components of the controller and stimulation means of the embodiment shown in FIG. 1.
Figure 19:
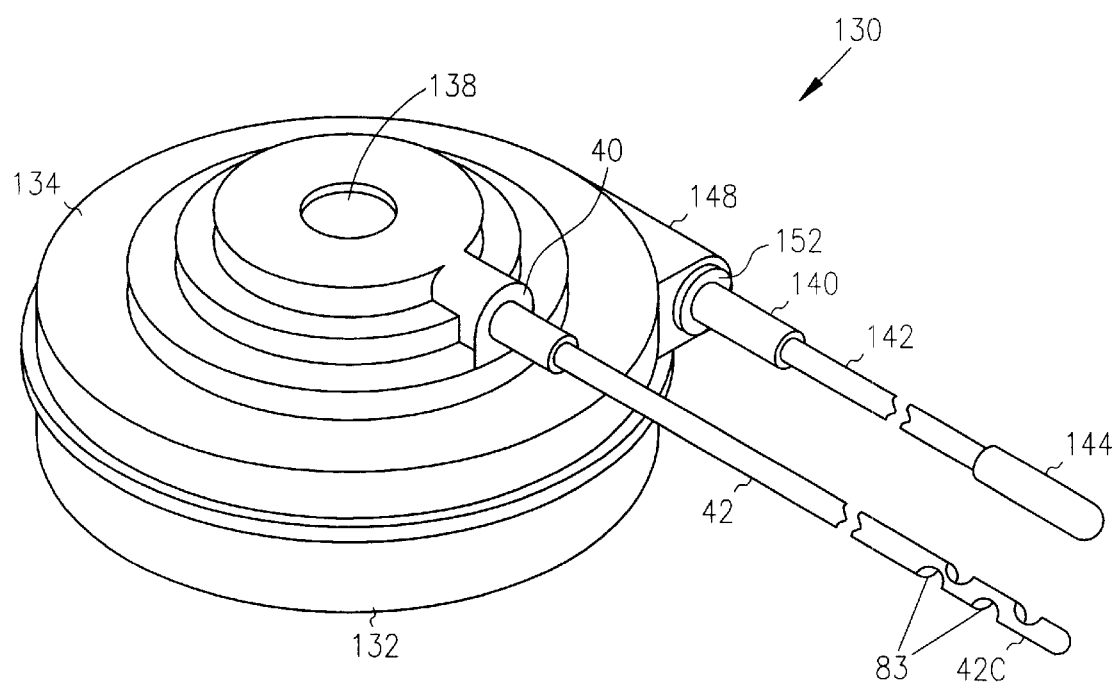
FIG. 19 is a generally perspective view of yet another form of the fluid delivery apparatus of the invention that is implantable within the patient's body.
Figure 20:
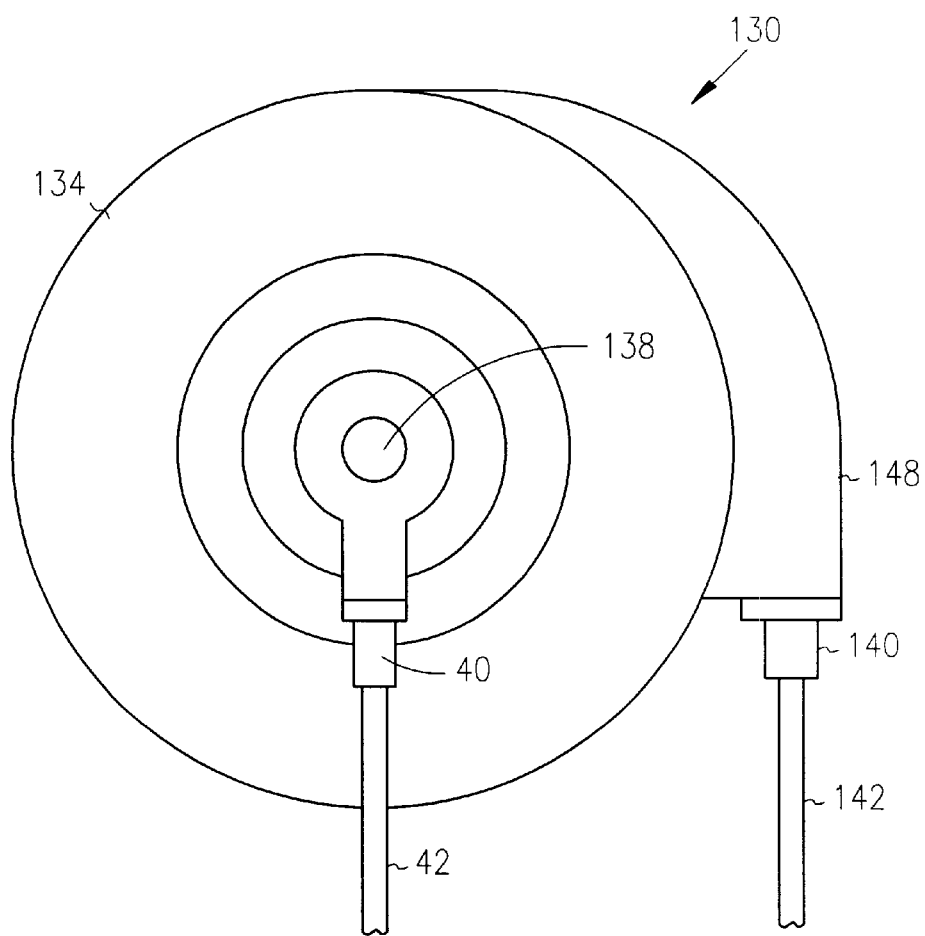
FIG. 20 is a top plan view of the apparatus shown in FIG. 19.
Figure 21:
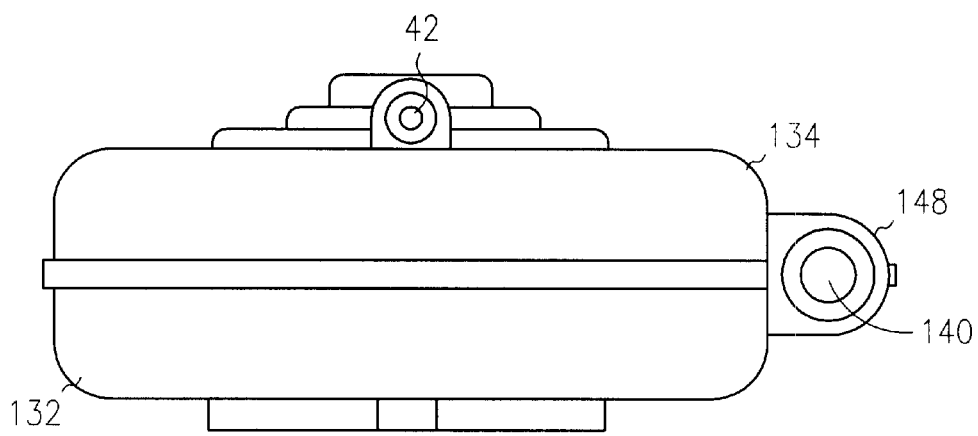
FIG. 21 is a side-elevational view of the apparatus shown in FIG. 20.
Figure 22:
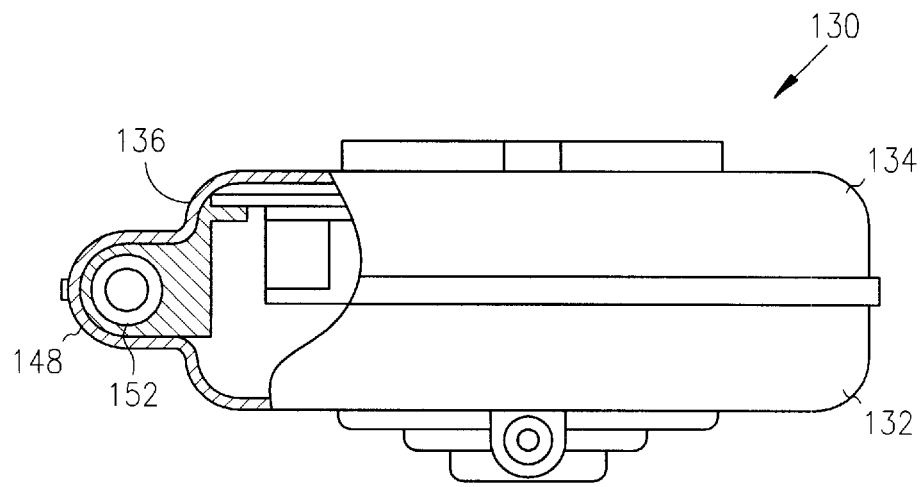
FIG. 22 is a side-elevational view of the apparatus partly broken away to show internal construction.
Figure 23:
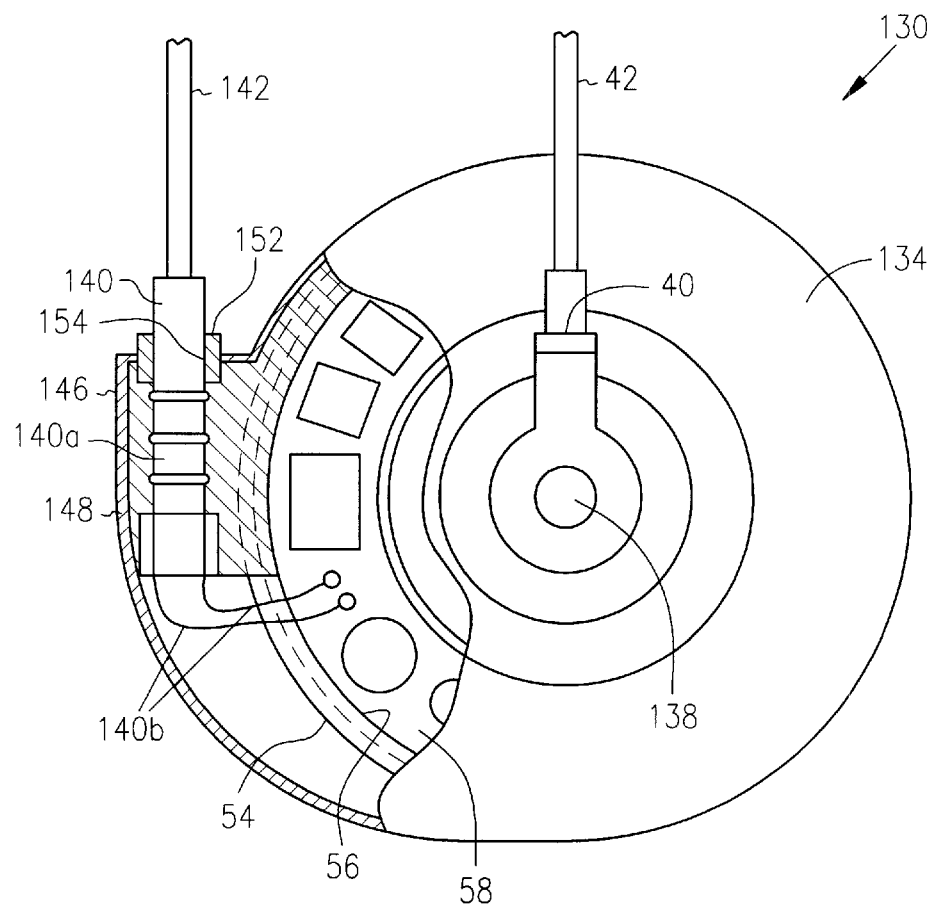
FIG. 23 is a top plan view of the apparatus partly broken away to show internal construction.
Figure 25:
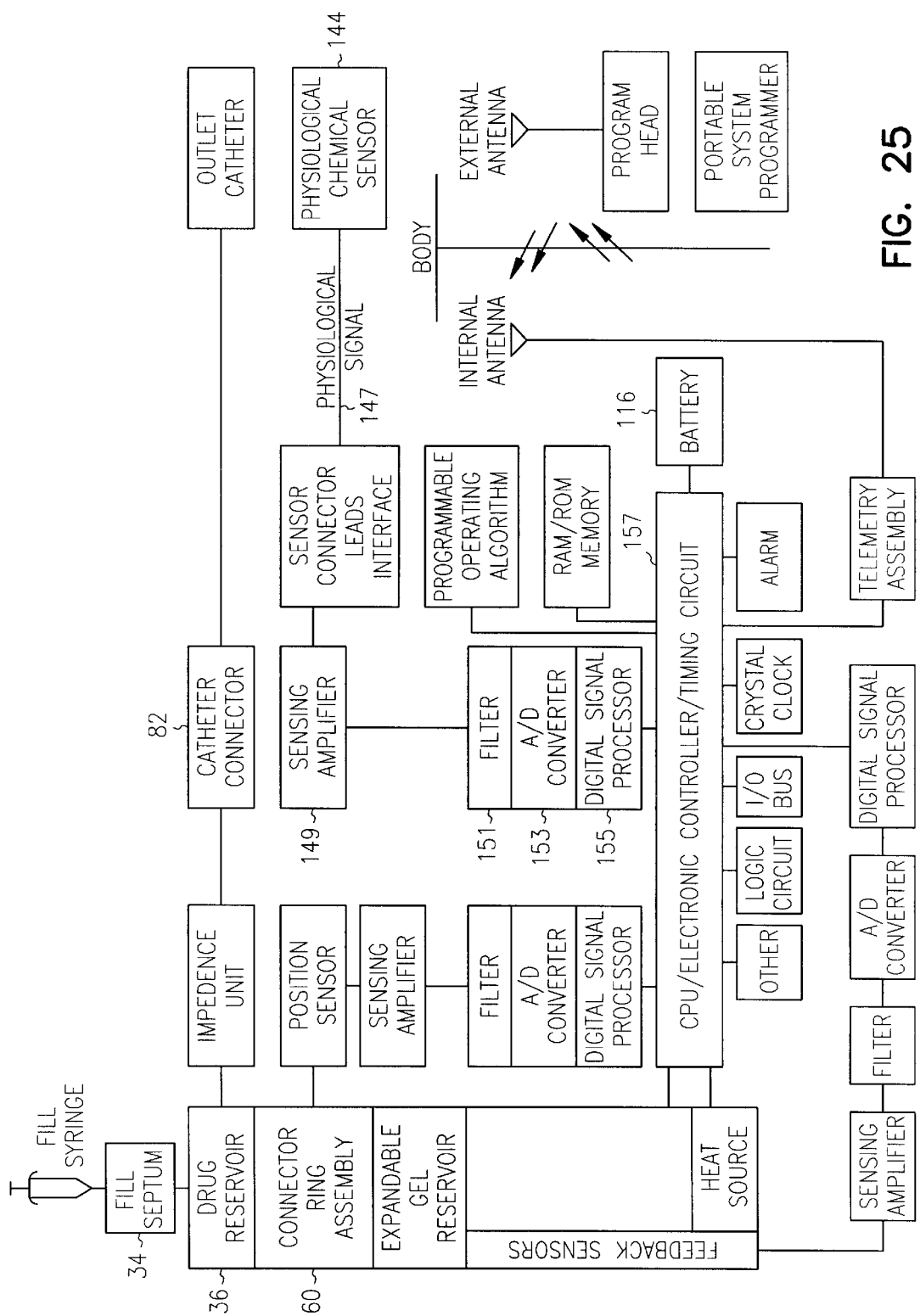
FIG. 25 is a generally diagrammatic view further illustrating the relationship among the major operating components of the apparatus including an implantable physiological sensor, system telemetry and external programming capability.

As shown in FIG. 18, the electronic controller comprises a central processing unit 112 having a memory 114 and a conventional power source such as a commercially available magnesium oxide or lithium battery 116 (FIG. 25). Also forming a part of the electronic controller is a heat control 118, a crystal clock 120 and appropriate telemetry 122.

Further details relating to the electronic controller and its relationship with the operating components of the delivery device, including a novel sensor means, the character of which will later be described, are shown in block diagram form in FIG. 25. More particularly, this figure shows the relative relationship among the fill means of the device, the fluid reservoir, the device gel reservoir, the heat source, the catheter and a reservoir position sensor. Additionally, FIG. 25 illustrates, in block diagram form, the relationship among these components and the various components and related systems that make up the electronics of the device including the central processing unit, the RAM/ROM memory, the digital signal processor, the logic circuit, and the telemetry assembly. As previously mentioned, the various electronic components of the device are well known to those skilled in the art and their interconnection and programming to meet the various requirements of the physician and patient protocol are well within the capability of the skilled artesan.

Upon filling the drug reservoir and after the electronic controller is initially programmed in a manner well understood by those skilled in the art, the device can be implanted into the patient. In the paragraphs that follow, the electronics as well as the method of programming the electronics will be further described.

At any time during the fluid delivery step, current flow to the heater wires 90a can be stopped by the controller and the expandable gel 46 will return to the less swollen configuration shown in FIG. 6. With the apparatus in the configuration shown in FIG. 6, fluid can be introduced into reservoir 36 in the manner previously described via septum 34 so that the apparatus will assume the configuration shown in FIG. 7. Upon the reheating of the heating means or heater wire 90a, the expandable gel will once again expand into the configuration shown in FIG. 8 causing fluid to be expelled from the device via cannula assembly 42.

Referring next to FIGS. 19 through 25, another form of the apparatus of the invention is there shown and generally designated by the numeral 130. This embodiment of the invention is similar in many respects to the embodiment shown in FIGS. 1 through 18 and like numerals are used in FIGS. 19 through 23 to identify like components. This latest embodiment is also designed to be implanted into the body of the patient in the manner previously described. As before the apparatus comprises a titanium base 132 and a titanium cover 134 that can be joined together as by welding to form the hollow housing 136 of the device. Unlike the embodiment of the invention shown in FIGS. 1 through 19, here the device uniquely includes integral, interactive sensor means and sensor connecting means for interconnecting the sensor with the device electronics disposed within housing 136.

The delivery device is adapted to be implanted within the patient's body at a location immediately below a layer of skin so that an access port 138 formed in the housing can be accessed by a hypodermic needle to introduce, in the manner previously described, a quantity of liquid medicament such as heparin, morphine, insulin or like medicament through a septum 34 into a drug reservoir. During operation, the medicament is delivered from the delivery device via a cannula port 40 to which a cannula assembly 42 is attached.

Housing 136 houses the novel heat activated stored energy source of the invention which functions to cause the fluids contained within the sealed reservoir of the device, the character of which will presently be described, to flow outwardly thereof through an outlet port of the character previously described that is formed in cover 134. As in the earlier described embodiments, the heat activated means or stored energy source, is provided in the form of a heat-activated, expandable polymer mass that is disposed within an expandable, hermetically sealed metal bellows assembly that is of the character previously described. The expandable mass is also of the same character as previously described herein. A carrier assembly 54 having an electronics receiving channel 56 supports an annular shaped PC board 58 (FIG. 23) and the electronic components associated therewith, the character of which are shown in FIG. 17 and which have previously been described.

Connected to and extending from cover 134 is the previously identified sensor means of the invention, for sensing various body conditions. The sensor means, which may comprise commercially available chemical, electro-chemical, and optical type sensors, here includes a connector 140, a conduit 142 and a sensor 144. Connector 140 includes a ribbed body portion 140a that is sealably receivable within an opening 146 formed in a protuberance that extends from the periphery of housing 136 in the manner shown in FIGS. 22 and 23. Conduit 142 extends through connector 140 and includes connector leads 140b that are connected to PC board 58 in the manner best seen in FIG. 23. A threaded connector 152 having an opening 154, is threadably received within opening 146 formed in protuberance 148. Connector 152, when snugged down, functions to maintain sensor connector 140 securely in position. The sensor tip 144 is appropriately positioned within the patient at the time of implantation of the delivery device.

Figure 24:
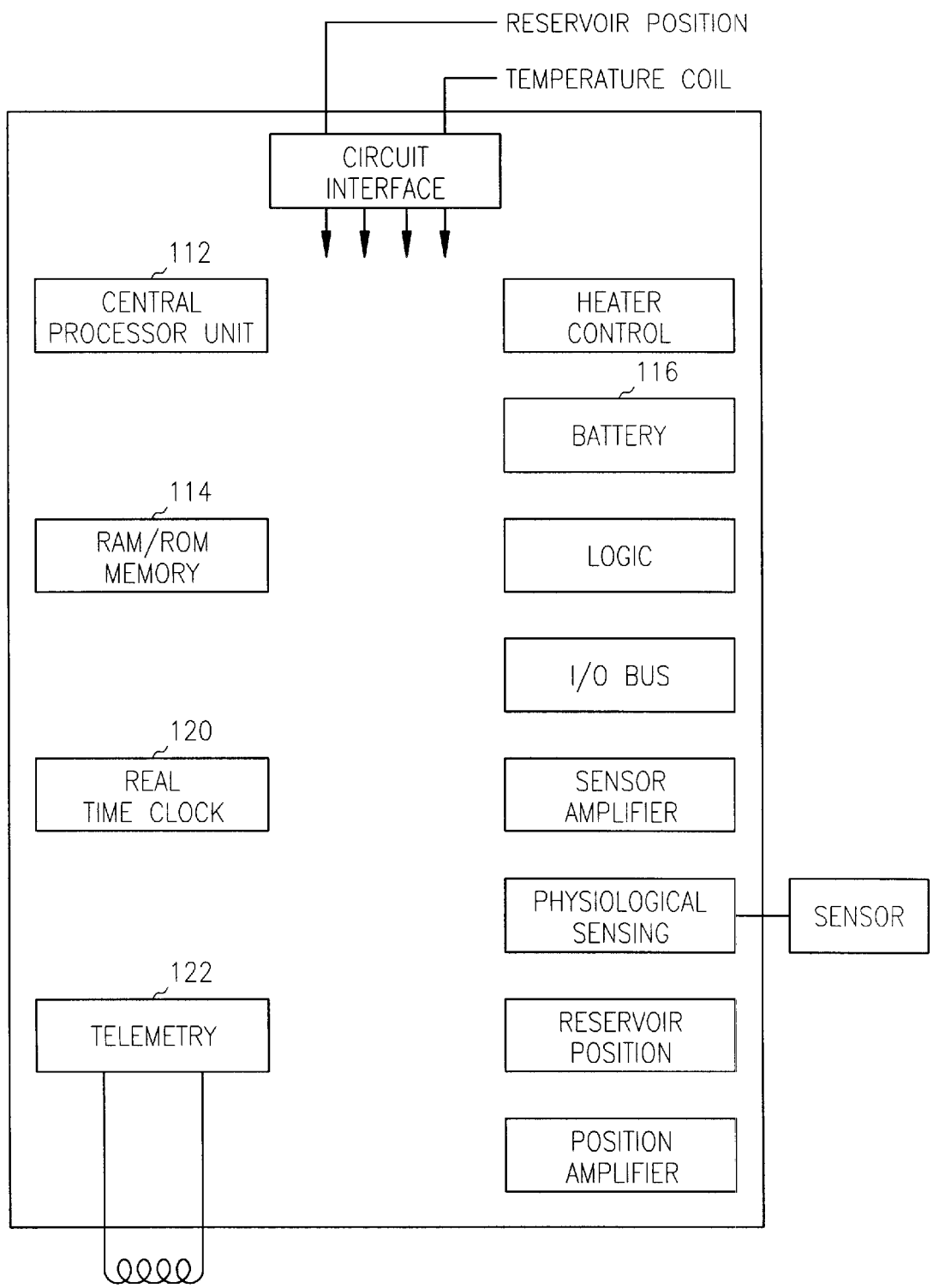
FIG. 24 is a generally diagrammatic view showing the relationship among the various components of the controller and stimulation means of the embodiment shown in FIG. 19.

As indicated in FIGS. 24 and 25, this latest embodiment of the invention uniquely comprises an In vivo, physiological sensing portion generally designated as 147 that is capable of detecting and responding to the physiological, physiochemical, chemical, optical and electronic changes in the body or bloodstream. The physiological sensing portion and its sensing structure may comprise an electronic, chemical or optical interface designed to measure specific parameters or changes in parameters and to compare known values combined within the associated delivery system electronic memory. It will be clear to those skilled in the art that, when the physiological sensing portion is coupled directly or indirectly with a sensing amplifier (FIG. 25) 149, with related filter 151, analog to digital converter 153, signal processor 155 and other sensing circuitry operating in conjunction with the programmable system electronics/CPU 157 that various physiological or chemical changes may be sampled and compared with known parameters set forth in a look-up table carried in device memory.

When necessary the CPU/electronic controller 157 can be programmed to execute a command function signal to initiate control and/or terminate the timed operation and frequency of light activation, pulse width duration and, when necessary, associated temperature circuitry. The resulting process is responsive to the physiological/chemical sensor circuitry and the output can be converted to digital signals and referenced against other controlling data will provide the interactive operating mode of operation of the delivery system.

Other suitably controlled sensors, which can measure bellows portion and displacement and related sensing circuitry, which comprise a part of the electronics of the apparatus, will also provide various signals including on/off function feedback signals for associated pulse logic sequences as well as position indication of the bellows connector ring assembly. Additionally, drug volume displacement, delivery rate over time measurements, battery life and system temperature and like data can be provided. Other alarm data can also be provided as, for example, reservoir condition and component malfunction. The telemetry assembly relies on the use of a radio frequency transmission system that is commercially available and well known to those skilled in the art. With the use of such a system, it is possible to up link the system performance, event history data residing in the receiving register and other operating parameters and current values such as the remaining drug volume and battery life.

Further the telemetry assembly can receive down link instructions upon proper interrogation and address confirmation in the programmable system operating mode. Such programming changes of function and operating values can be implemented and recorded within the delivery system electronics controller memory. This program can also be accomplished through the use of an operably associated portable system programmer and programming head which can be readily adapted from commercially available systems that are well known to those skilled in the art.

Figure 26:
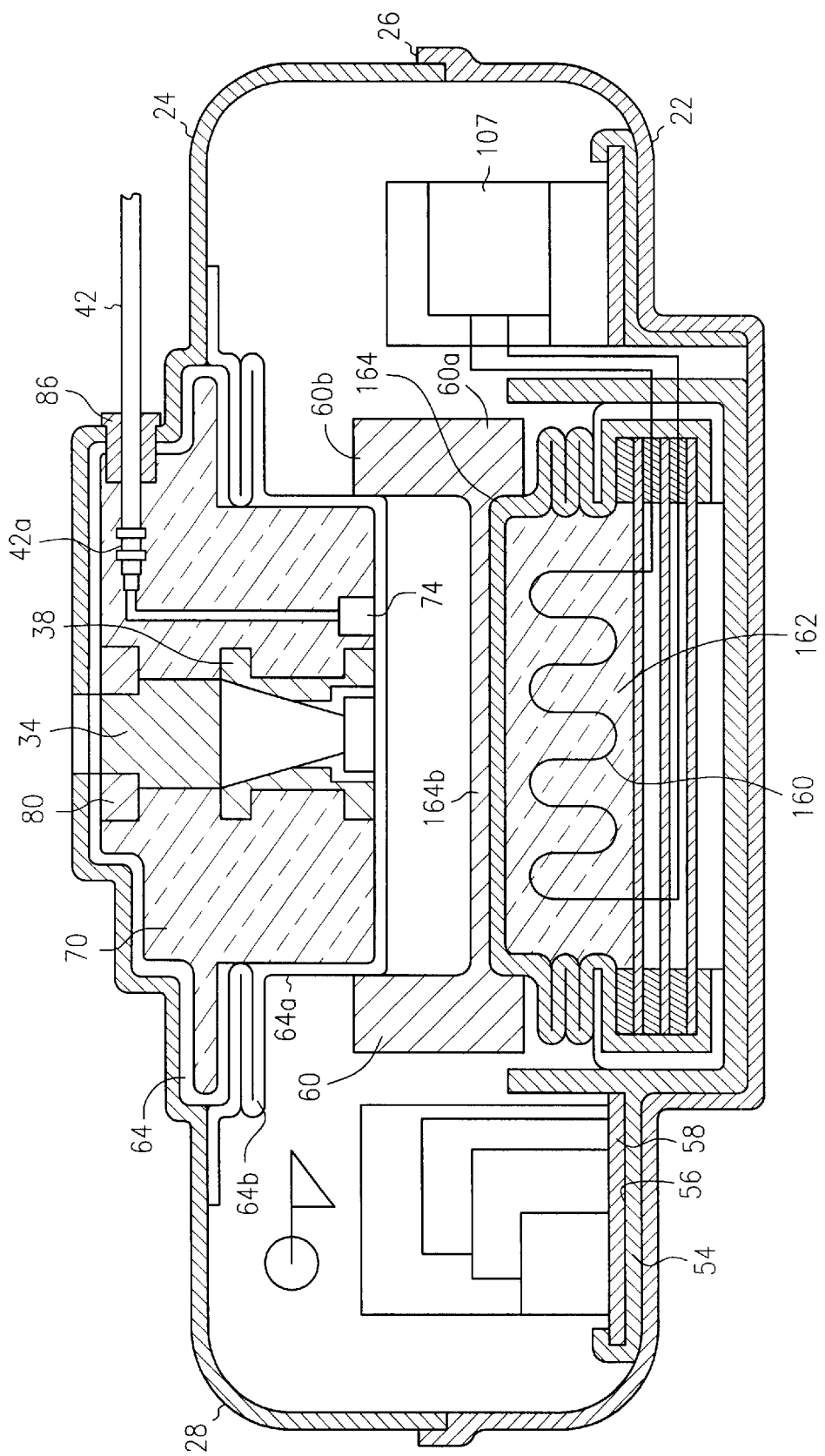
FIG. 26 is a cross-sectional view similar to FIG. 6, but showing still another form of the invention in which the heater coil is disposed within the expandable mass and in which the heater coil is energized by a radio-frequency generator.

Turning now to FIGS. 26 through 36, still another form of the apparatus of the invention is there shown. This embodiment of the invention is also similar in most respects to the embodiment shown in FIGS. 1 through 18 and like numerals are used in FIGS. 26 through 36 to identify like components. The principal difference between the embodiment shown in FIGS. 26 through 36 and the earlier described embodiment illustrated in FIGS. 1 through 18 concerns the positioning of the heater coil within the expandable mass and the novel manner in which the heater coil is energized. More particularly, as best seen in FIG. 26, in this latest embodiment of the invention the heater coil 160 is disposed within the expandable mass 162 which, in turn, is mounted within an expandable structure or bellows assembly 164.

This latest embodiment is also designed to be implanted into the body of the patient in the manner previously described. As before the apparatus comprises a titanium base 22 and a titanium cover 24 that can be joined together as by welding to form the hollow housing 28 of the device. It is to be understood that the device of this last embodiment of the invention can, if desired, be modified to also include integral, interactive sensor means and sensor connecting means of the character previously described (see FIGS. 35 and 36).

Figure 31:
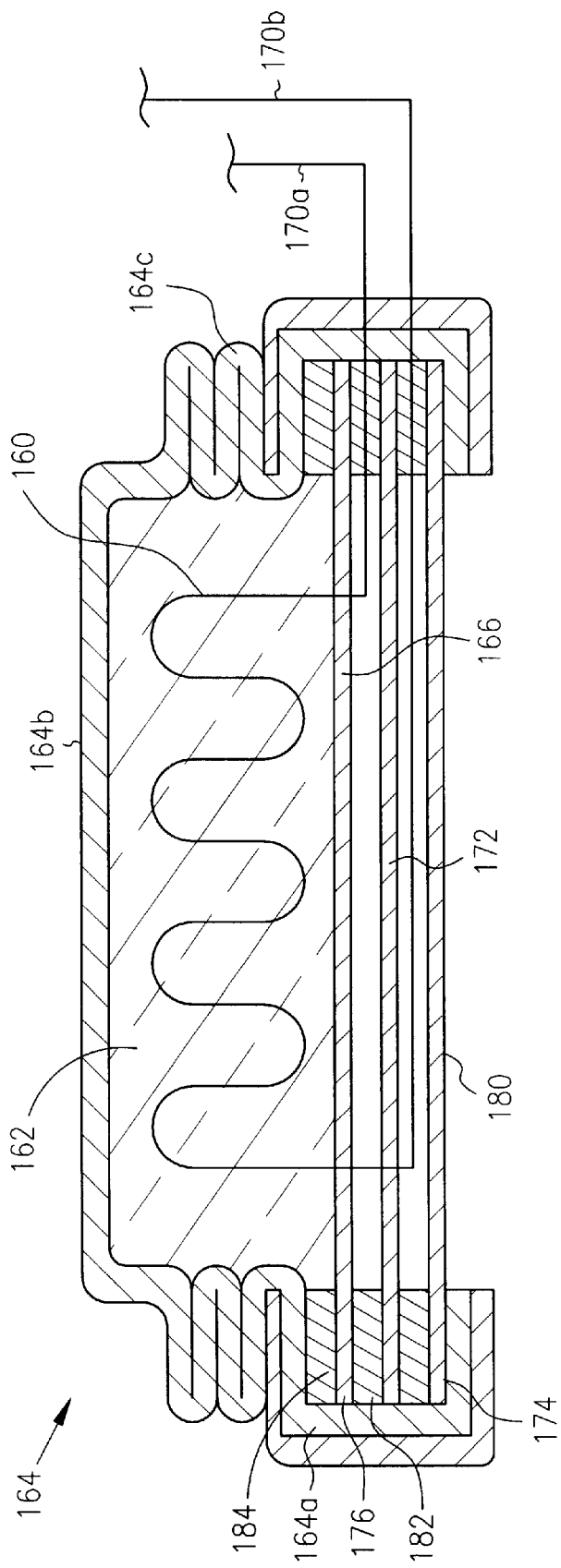
FIG. 31 is a cross-sectional view of the bellows assembly that houses the expandable gel and the heater coil of the apparatus.
Figure 32:
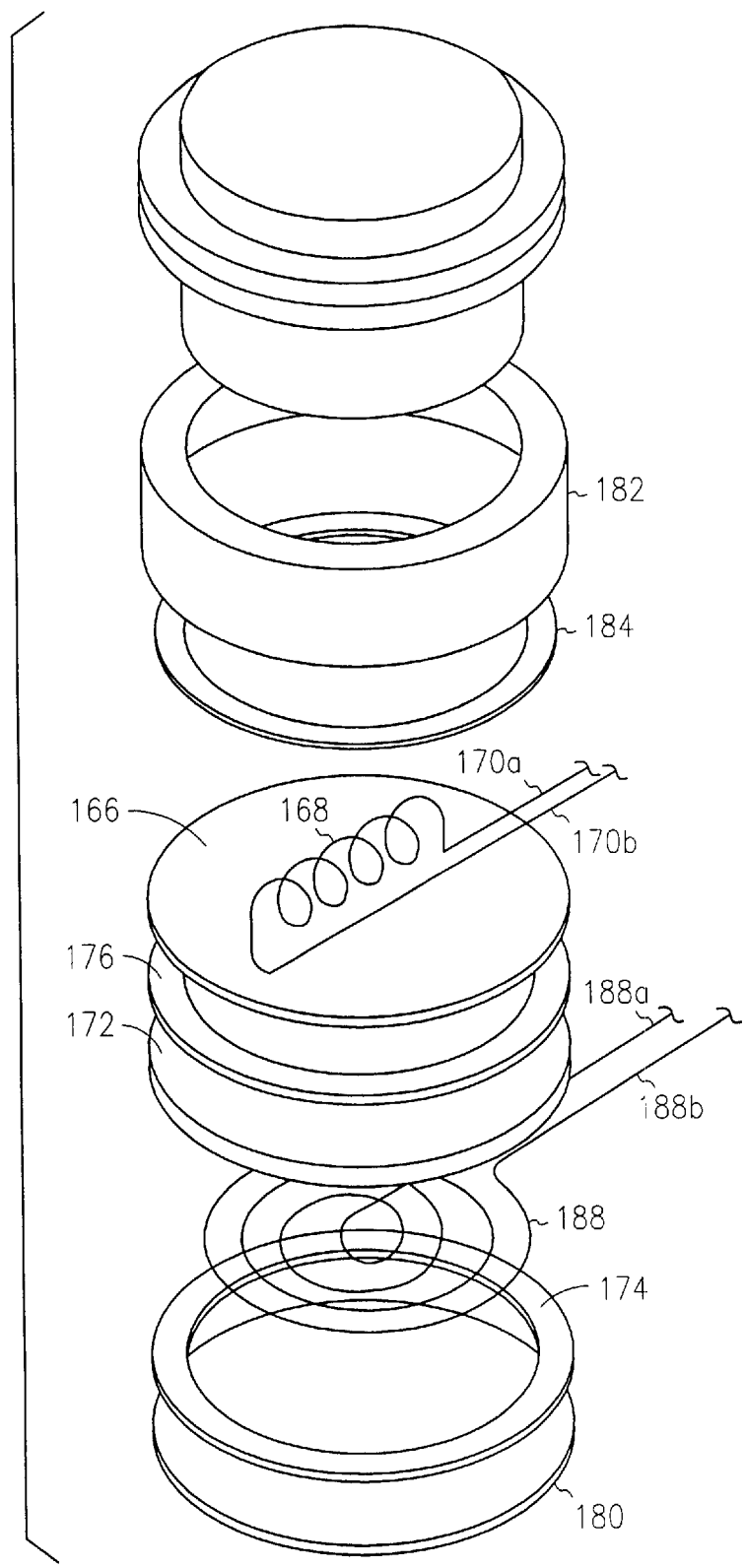
FIG. 32 is a generally perspective, exploded view of the assembly shown in FIG. 31.
Figure 33:
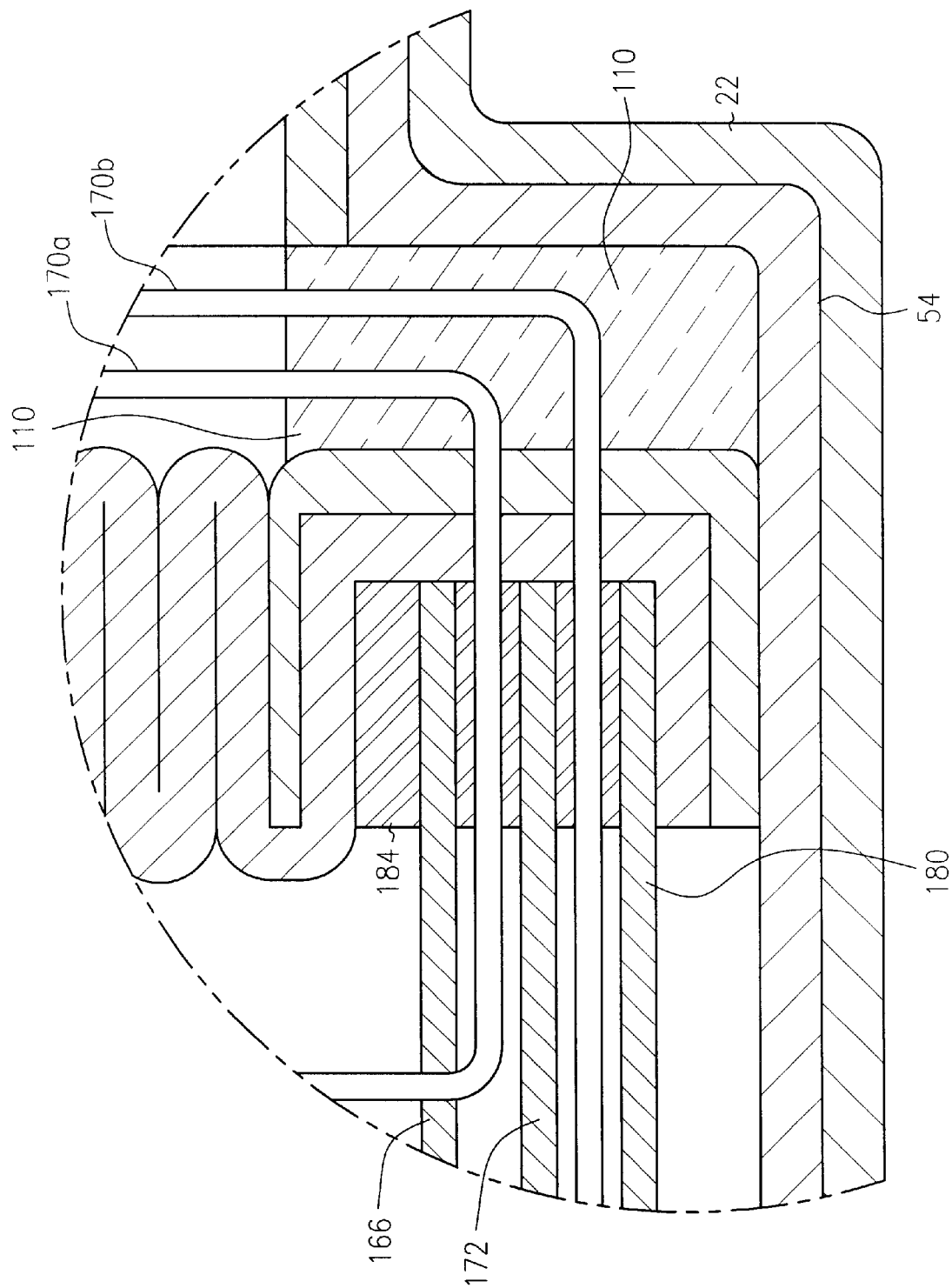
FIG. 33 is an enlarged, cross-sectional view of the area designated in FIG. 27 as 33.
Figure 34:
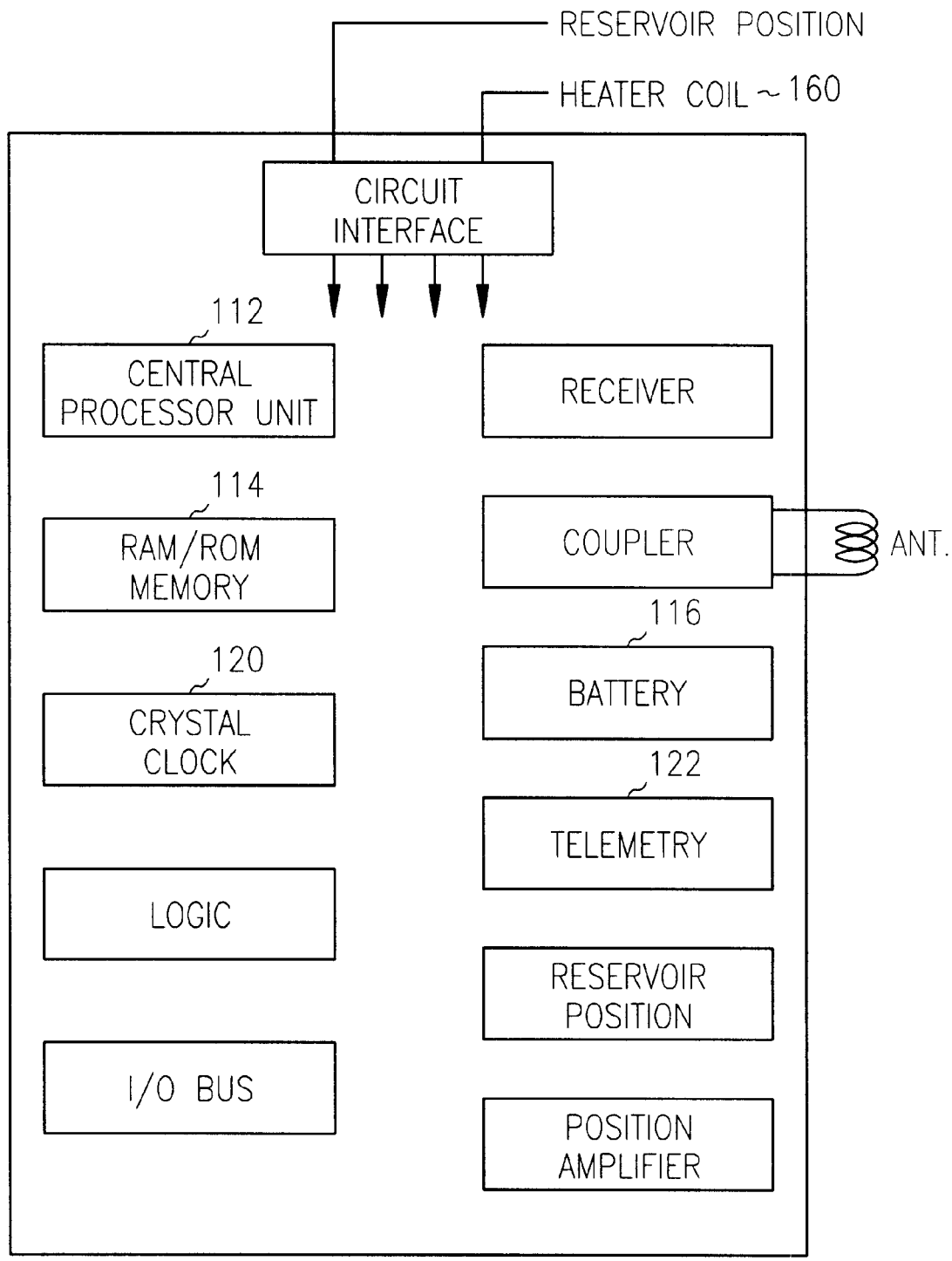
FIG. 34 is a generally diagrammatic view showing the relationship among the various components of the controller and stimulation means of the embodiment shown in FIG. 26.

As best seen in FIGS. 31 and 32, the bellows assembly 164 includes a base portion 164a, an upstanding, reduced diameter cover 164b and an expandable bellows-like sidewall 164c which are interconnected to define the gel-receiving chamber 167. Bellows assembly 164 is closely received within a receiving chamber 52 formed in a carrier assembly 54, which is of identical construction to that previously described.

As before an electronics receiving channel 56 surrounds chamber 167. Channel 56 supports an annular shaped, printed circuit (PC) board 58 and the electronic components associated therewith, which are also of the character previously described. Upstanding cover 164b of bellows assembly 164 is closely received within the lower portion 60a of a generally annular shaped capture ring 60 which is of the same construction earlier described herein.

Base portion 64a of an expandable structure, which forms the upper reservoir assembly 64 of the apparatus, is receivable within the upper portion 60b of the capture ring 60. Upper reservoir assembly 64 is also of identical construction and operation to that previously described and illustrated in FIG. 7.

Considering next the activating means of this latest embodiment of the invention for activating the expandable mass or gel 162, this novel means here comprises a radio frequency energized source of heat that includes heater plate 166 upon which is mounted a transversely extending heater coil 160, both of which are carried within bellows assembly 164. Connected to heater coil 160 are a pair of wire leads 170a and 170b, the purpose of which will presently be described. As best seen in figures 31 and 32 heater plate 166 is supported by a ceramic heat deflector 172, which, in turn, is supported by a silicone ring seal 174. A second silicone ring seal 176 is disposed between heat deflector 172 and heater plate 166. A closure plate 180 is connected to base 164a of bellows 164, as by welding, to sealably encapsulate the activating means (FIG. 31). A bellows clamp ring 182 circumscribes the lower portion of the bellows assembly in the manner earlier described and as indicated in FIGS. 31 and 32. To sealably position heater plate 166 within the bellows assembly, a third silicone seal ring 184 is disposed between the upper surface of heater plate 166, bellows 164 (see FIG. 32).

Figure 29:
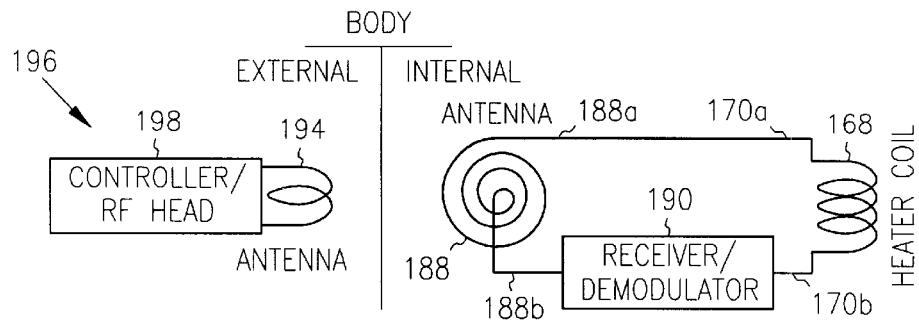
FIG. 29 is a generally schematic view illustrating the positioning of the gel heating means within the patient's body and the positioning of the radio-frequency generator means outside the patient's body.
Figure 30:
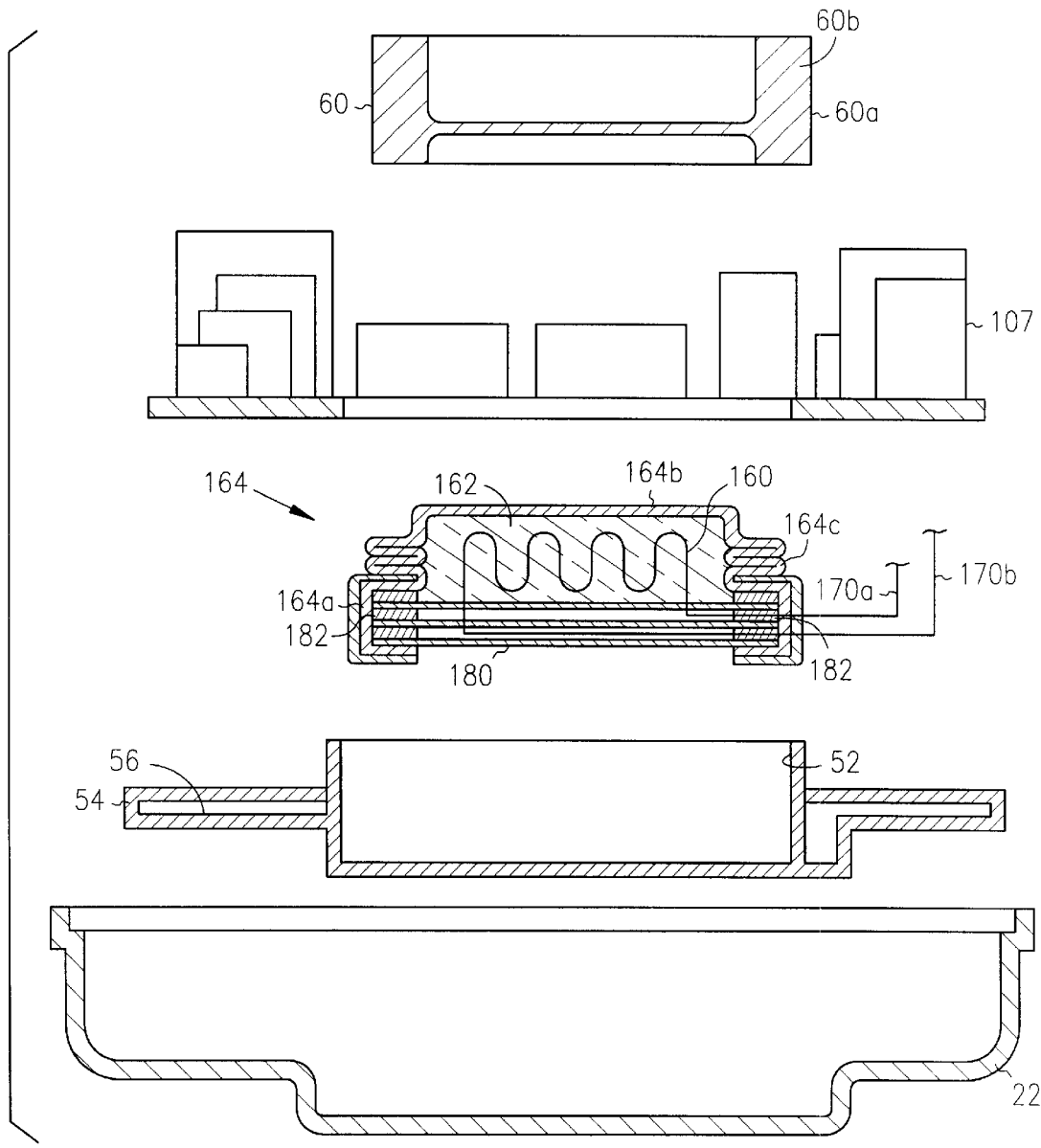
FIG. 30 is an exploded, cross-sectional view of the lower half shell of the apparatus of this latest form of the invention that houses the carrier assembly, the connector ring, the bellows assembly, the expandable gel, the gel-heating means, and the electronics associated therewith.

Disposed between ceramic heat deflector 172 and base plate 180 is antenna means shown here as spiral shaped power receiving antenna 188 for receiving power from the radio frequency transmitting means of the invention, the character of which will be described hereinafter (FIG. 32). As indicated in FIG. 29, leads 188a and 188b are operably interconnected with heater coil leads 170a and 170b. More particularly, lead 188a is connected to heater coil lead 170a, while lead 188b is connected to heater coil lead 170b via a conventional RF receiver/demodulator 190. RF receiver/demodulator190 is of a character well known in the art and various commercially available components can be readily modified to meet present requirements.

Antenna 188 is also of a character well known to those skilled in the art and is configured for receiving electrical power from the frequency transmitting means that here comprises a transmitting antenna 194. As indicated in FIG. 29, antenna 194 transmits power to antenna 188 through induction coupling. Antennas, such as antenna 188, are well known in the art and are of the same general character as those used in connection with implanted pacemakers and like devices.

Figure 36:
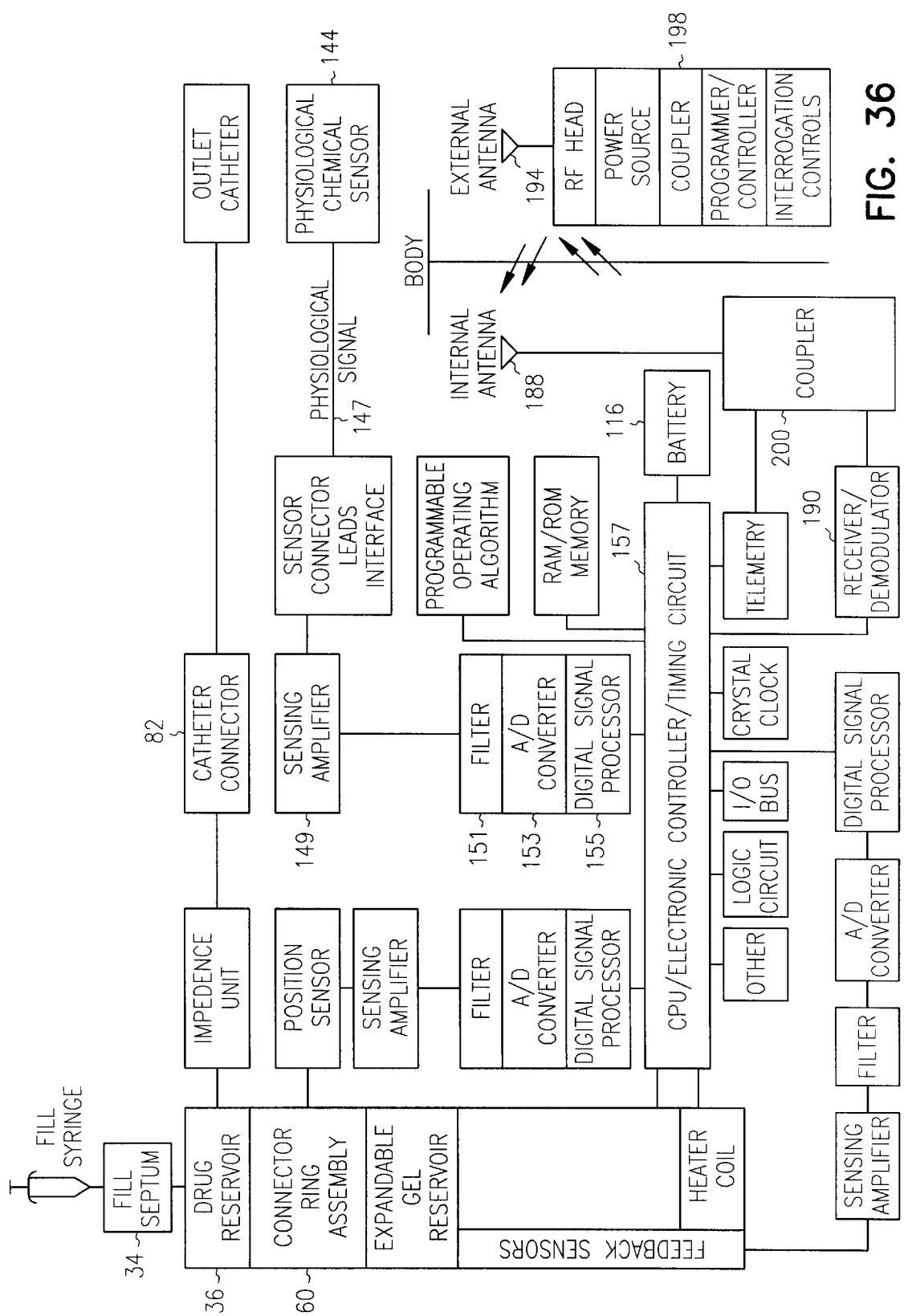
FIG. 36 is a generally diagrammatic view further illustrating the relationship among the major operating components of the apparatus illustrated in FIG. 26 including the physiological sensor, the system telemetry and the external programming.

The frequency transmitting means, or power unit 196, which, is located externally of the patient, includes transmitting antenna 194, which is operably connected to a controller/RF head 198 of conventional construction. In one form of the invention, power unit 196 is operable to produce radio frequencies in the range of 3 to 30 MHZ so that when antenna 194 is positioned proximate antenna 188 and is inductively coupled therewith, power can be delivered to heater coil 160 with very little loss and can be accomplished transdermally (see FIG. 29). Additionally, controller/RF head 198 transmits various control telemetry information to the CPU electronic controller 157 via a coupler 200 and telemetry 204 (FIG. 36). In a manner well understood by those skilled in the art, controller 198 allows selective control of the amplitude and timing of the output enabling selective control over the heating of heater coil 160.

Figure 27:
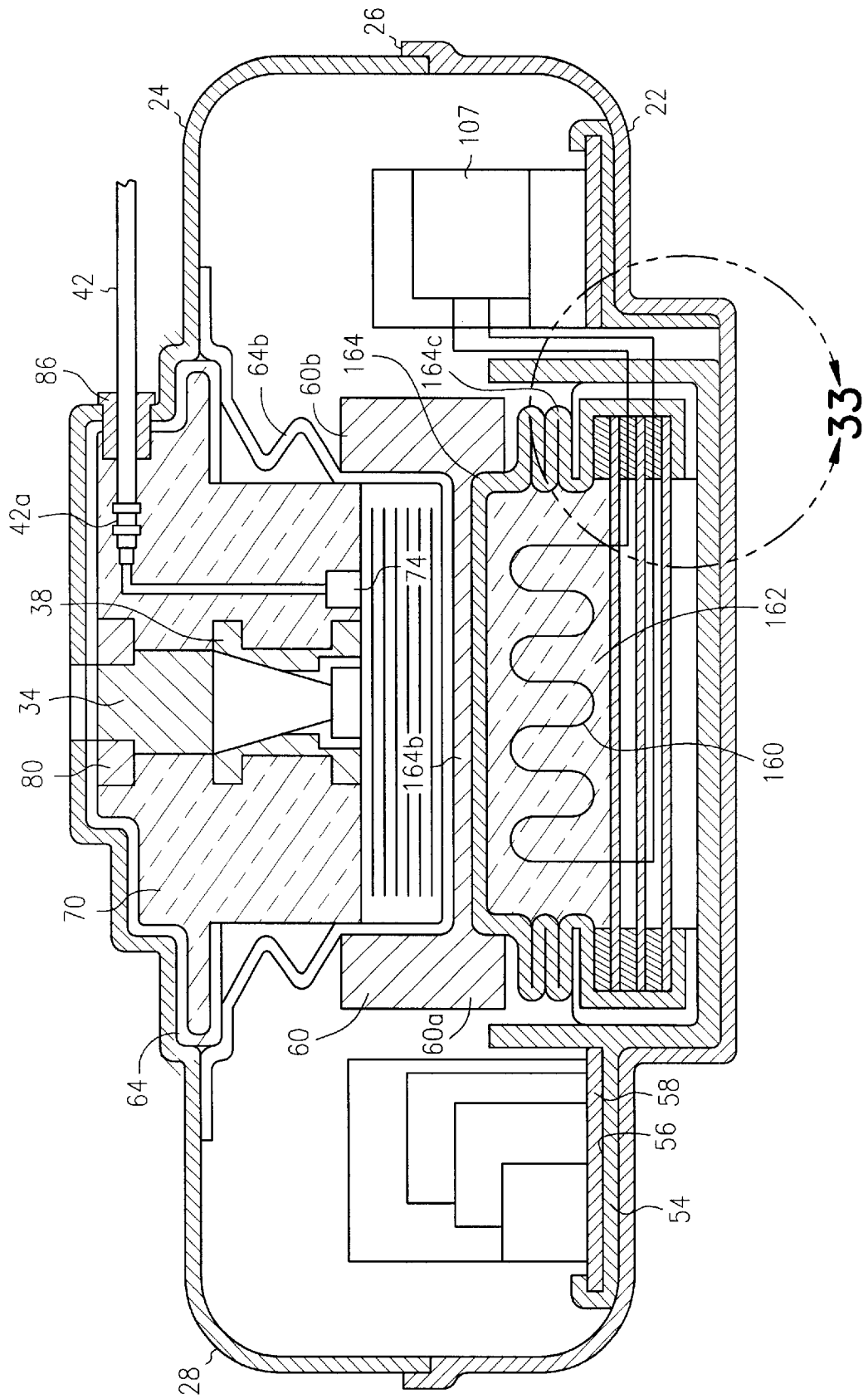
FIG. 27 is a cross-sectional view similar to FIG. 26, but showing the reservoir of this latest embodiment in a filled condition.
Figure 28:
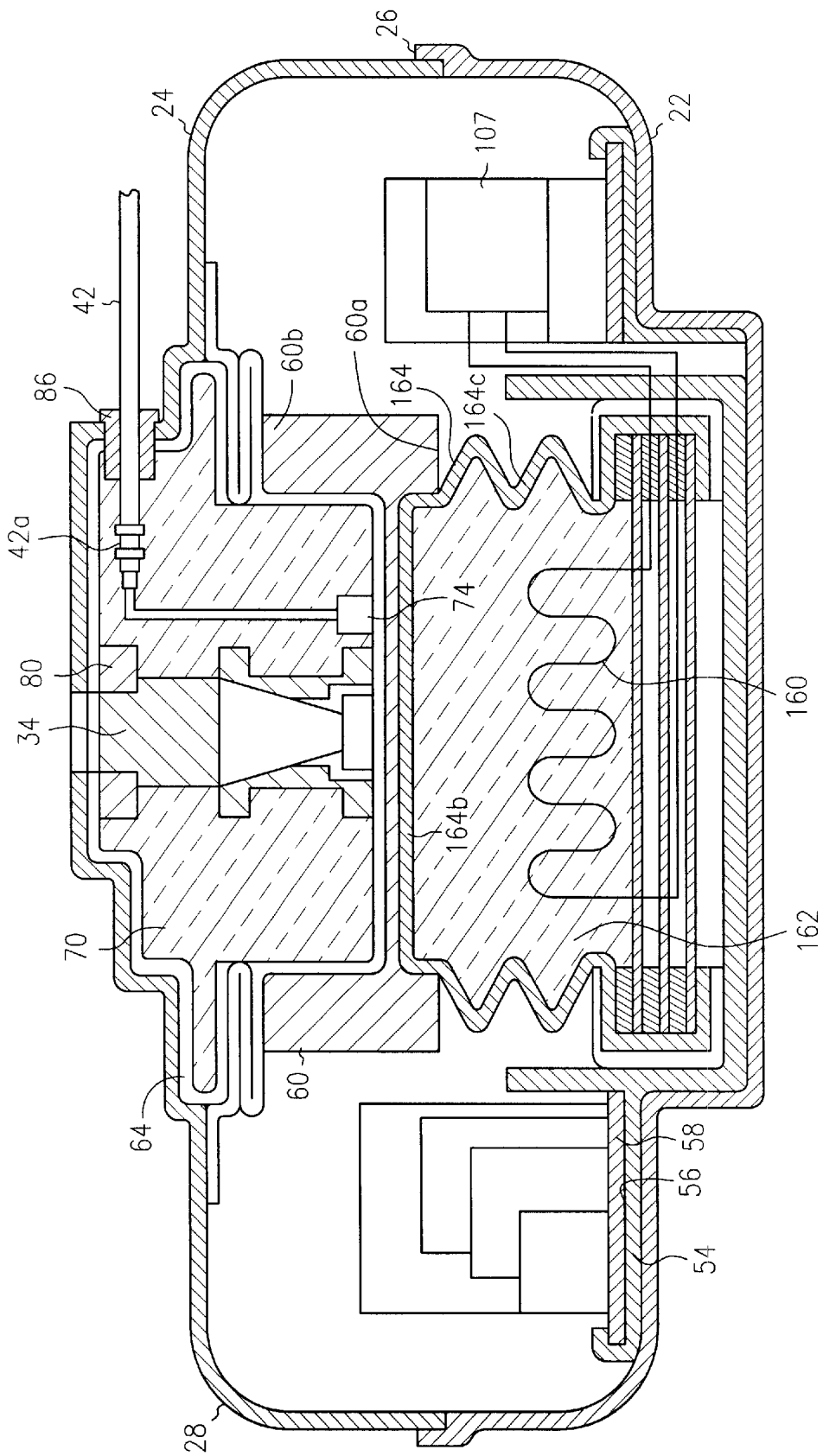
FIG. 28 is a cross-sectional view similar to FIG. 27, but showing the expandable gel in an expanded configuration following delivery of all of the medicament to the patient.

With the construction described in the preceding paragraphs, the controlled heating of heater coil 160, which is embedded within expandable mass 162 in the manner shown in FIGS. 26, 27 and 28, will controllably heat the expandable mass or gel 162 to cause the controlled expansion thereof. With the apparatus in the configuration shown in FIG. 28, fluid can be introduced into reservoir 36 in the manner previously described via septum 34 so that the apparatus will assume the configuration shown in FIG. 27. Upon heating the heater coil 160, the expandable gel 162 will expand into the configuration shown in FIG. 28 causing fluid to be expelled from the device via cannula assembly 42. It should be understood that a contracting gel and an appropriately modified bellows structure can also be said to controllably expel fluid from the fluid reservoir of the device.

Figure 35:
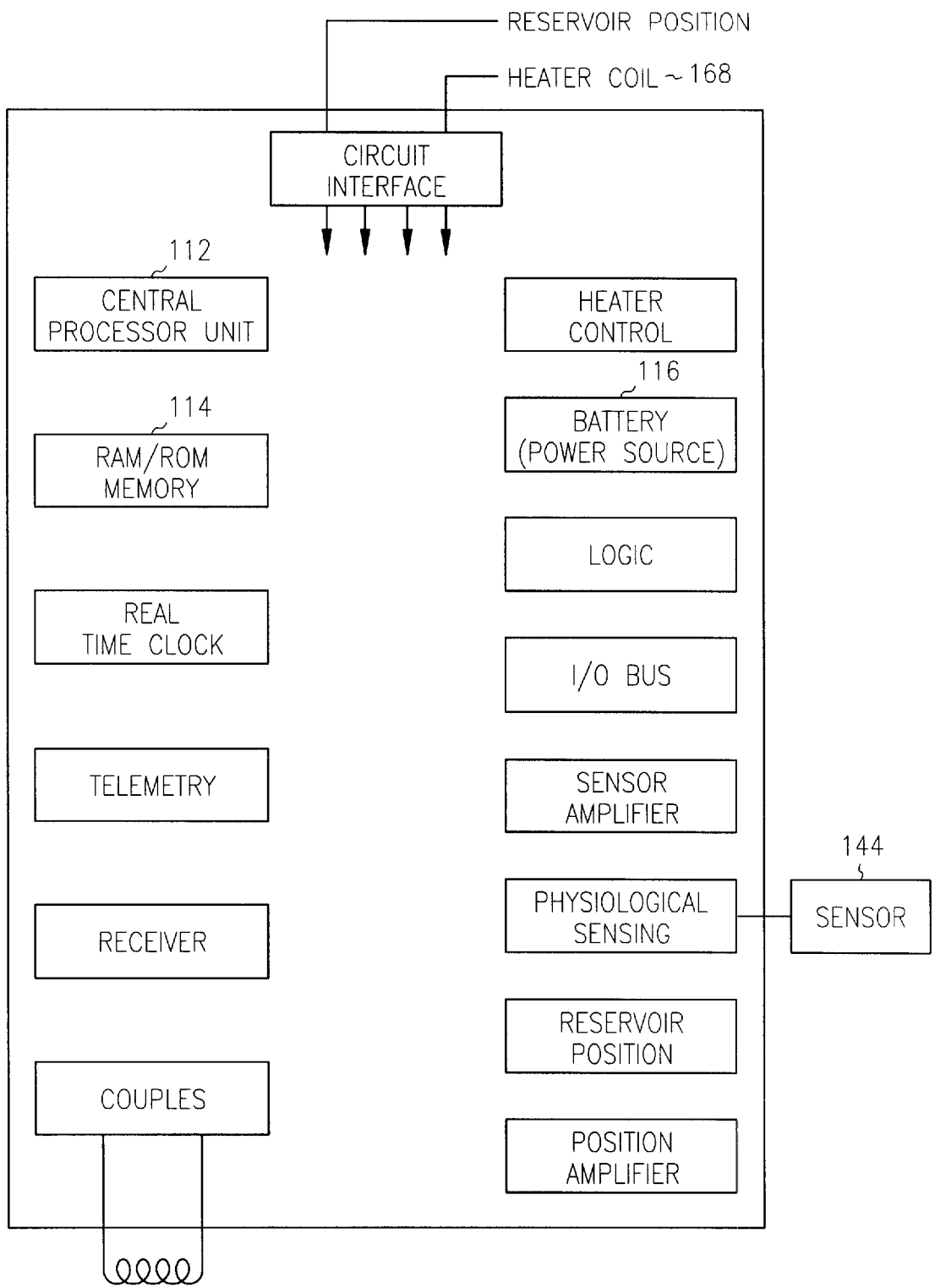
FIG. 35 is a generally diagrammatic view of an alternate form of the apparatus shown in FIG. 26 illustrating the relationship among the various components of the controller, the stimulation means and the sensor means of the alternate embodiment of FIG. 26.

In using the apparatus of this latest form of the invention, either before or after the reservoir has been filled in the manner shown in FIG. 27, the electronic controller which is of the character previously described can be programmed (see FIGS. 35 and 36). In the present form of the invention, the electronic controller comprises a central processing unit 112 having a memory 114 and a conventional power source such as a commercially available magnesium oxide or lithium battery 116. Also forming a part of the electronic controller is a crystal clock 120 and appropriate telemetry 122. Further details relating to the electronic controller and its relationship with the operating components of the delivery device, can also be seen by referring to FIG. 36. More particularly, this figure shows the relative relationship among the fill means of the device, the fluid reservoir, the device gel reservoir, the antenna systems, the catheter and the programmable sensor.

As indicated in FIGS. 35 and 36, sensor means of the character previously described, can be added to the latest embodiment of the invention. This sensor means is of identical construction and operation to that previously described and is interconnected with the implantable device shown in FIGS. 26 through 33 in the manner schematically illustrated in FIGS. 35 and 36.

As previously discussed herein, polymeric gels that respond to various physical and chemical stimuli by expanding or contracting as a result of the applied stimuli, are well documented in the patent and academic literature (see for example, Tanaka et al. U.S. Pat. No. 5,100,933 and Responsive Gels Vols. 1 & 2, K. Dusek, Ed., Springer-Verlag, 1993). Polymeric gels such as acrylamides, acrylic acids and poly (alkyl ethers) have been shown to reversibly swell due to a change in temperature. The factors that control these volume phase changes, which can be greater than 300 times the original volume, have been attributed to Vander Waals, hydrophobic-hydorphilic and hydrogen bonding forces. Further, depending on the fluid medium encapsulated by the gel (both in terms of chemical composition and concentration), the chemical composition of the gel and any additional chemical additives (such as a second polymer species, as in the case of an interpenetrating polymer network) the gel can expand or contract at its phase transition temperature (Responsive Gels Vols, 1 & 2, K. Dusek, Ed., Springer-Verlag, 1993). Additionally, it is well known that the expansion (or contraction) of thermally responsive gels can be continuous or discontinuous, depending on the properties mentioned above.

Thus, for the implantable devices described herein, a thermally responsive gel can be used as the stored energy means capable of doing work once made to expand (or contract) by the application of thermal energy in the various manners previously described herein. In the case of the last described embodiment where the heater coil is coupled with a radio frequency receiving antenna, the expansion or retraction of the gel and the concomitant release of the drug can be uniquely activated by a remote control device such as power unit 196.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. An implantable device for implantation within a patient for infusing medicinal fluid into the patient at a controlled rate comprising:

(a) a housing having an outlet;

(b) a fluid reservoir containing a fluid disposed within said housing, said fluid reservoir having an inlet and an outlet in communication with said outlet of said housing;

(c) a heat stimulated mass disposed within said housing proximate said reservoir, said mass comprising a semi-solid, which upon being stimulated, will act upon said fluid within said reservoir to cause said fluid to flow outwardly of said outlet of said reservoir; and (d) stimulation means for stimulating said mass, said stimulation means comprising a source of heat.

2. The device as defined in claim 1 in which said mass is disposed within an expandable structure disposed within said housing.

3. The device as defined in claim 1 further including means for forming said reservoir said means comprising a second expandable structure disposed within said housing.

4. The device as defined in claim 1 in which said mass comprises a gel.

5. The device as defined in claim 1 further including a cannula connected to said housing and communicating with said reservoir for delivering fluid from said reservoir to the patient.

6. The device as defined in claim 1 further including an ullage disposed within said housing and located proximate said fluid reservoir.

7. The device as defined in claim 1 in which said stimulation means comprises a heat plate disposed proximate said mass.

8. The device as defined in claim 1 further including fill means in communication with said reservoir for filling said reservoir.

9. The device as defined in claim 8 in which said housing comprises a base and a cover superimposed over said base and in which said fill means comprises a septum disposed within said cover, said septum being pierceable by a cannula inserted into said septum.

10. An implantable device for implantation within a patient for infusing medicinal fluid into the patient at a controlled rate comprising:
   (a) a housing having an outlet;
   (b) a fluid reservoir containing a fluid disposed within said housing, said reservoir having an inlet and an outlet in communication with said outlet of said housing;
   (c) a heat stimulated, expandable polymer gel disposed within said housing, said polymer gel upon being stimulated, expanding to act upon said fluid within said reservoir to cause said fluid to flow outwardly of said outlet of said reservoir; and
   (d) stimulation means for stimulating said polymer gel, said stimulation means comprising a source of heat.

11. The device as defined in claim 10 in which said polymer gel is contained within an expandable structure disposed within said housing.

12. The device as defined in claim 10 further including a second expandable structure disposed within said housing, said fluid reservoir being formed by said second expandable structure.

13. The device as defined in claim 10 in which source of heat comprises a heater wire.

14. The device as defined in claim 10 in which said source of heat comprises first and second heater plates and a heater wire disposed between said heater plates.

15. The device as defined in claim 10 further including a flow controlling impedance frit disposed between said fluid reservoir and said outlet of said housing.

16. The device as defined in claim 10 further including a delivery cannula connected to said outlet of said housing for delivery of fluid to the patient.

17. The device as defined in claim 10 further including sensor means connected to said housing for detecting changes in the patient's body.

18. The device as defined in claim 10 further including fill means in communication with said reservoir for filling said reservoir.

19. The device as defined in claim 10 in which said polymer gel undergoes a change in polymer conformation upon being stimulated by said stimulation mass.

20. A medical device for implantation within a patient for infusing medicinal fluid into the patient at a controlled rate comprising:
   (a) a housing having an outlet;
   (b) a fluid reservoir containing a fluid disposed within said housing, said reservoir having an inlet and an outlet in communication with said outlet of said housing;
   (c) a heat stimulated, swellable polymer disposed within said housing proximate said reservoir, said polymer, upon being stimulated, swelling so as to act upon said fluid within said reservoir to cause said fluid to flow outwardly of said outlet of said reservoir;
   (d) stimulation means for stimulating said expandable polymer, said stimulation means comprising a source of heat; and
   (e) delivery means connected to said outlet of said housing for delivering fluid to the patient.

21. The device as defined in claim 20 in which said polymer comprises a phase transition polymer gel.

22. The delivery devices defined in claim 20 in which said delivery means comprises an elongated cannula having a first end connected to said outlet of said housing and a second end terminating in a porous tip.

23. The device as defined in claim 20 in which said polymer is contained within an expandable structure disposed within said housing.

24. The device as defined in claim 20 further including a second expandable structure disposed within said housing, said fluid reservoir being formed by said second expandable structure.

25. The device as defined in claim 20, further including interactive sensor means connected to said housing for sensing physiological changes in the patient.

26. The device as defined in claim 20 further including fill means carried by said housing for filling said reservoir.

27. The device as defined in claim 26 in which said fill means comprises a septum carried by said housing, said septum being pierceable by a cannula inserted into said septum.

28. An implantable device for infusing medicinal fluid into the patient at a controlled rate comprising:
   (a) a housing having an outlet, said housing being implantable within the body of the patient;
   (b) a fluid reservoir containing a fluid disposed within said housing, said fluid reservoir having an inlet and an outlet in communication with said outlet of said housing;
   (c) a heat stimulated, expandable mass disposed within said housing proximate said reservoir, said expandable mass comprising a semisolid, which upon being stimulated, will act upon said fluid within said reservoir to cause said fluid to flow outwardly of said outlet of said reservoir; and
   (d) stimulation means for stimulating said expandable mass, said stimulation means comprising:
      (i) a heating coil disposed within said housing proximate said expandable mass; and
      (ii) means disposed outside the patient's body for heating said heating coil.

29. The device as defined in claim 28 in which said means for heating said coil comprises:
   a. a first antenna coupled with said heating coil; and
   b. radio frequency transmitting means, including a second antenna disposed proximate said first antenna for controllably heating said heating coil.

30. The device as defined in claim 29 in which said radio frequency transmitting means includes a controller.

31. The device as defined in claim 28 in which said polymer gel is contained within a first expandable bellows disposed within said housing.

32. The device as defined in claim 28 further including a second expandable bellows disposed within said housing and operably associated with said first expandable bellows, said fluid reservoir being formed by said second expandable bellows.

33. The device as defined in claim 28 further including fill means carried by said housing for filling said reservoir.

* * * * *